United States Patent
Ratner et al.

(10) Patent No.: US 11,324,942 B2
(45) Date of Patent: May 10, 2022

(54) MEDICAL DEVICES INCLUDING ROTARY VALVE

(71) Applicant: University of Iowa Research Foundation, Iowa City, IA (US)

(72) Inventors: Albert Ratner, Iowa City, IA (US); Gurjap Singh, Iowa City, IA (US); Jay K. Bhama, Iowa City, IA (US)

(73) Assignee: ALBERT RATHER, JAY K. BRAMA, MD, GURJAP SINGH, Iowa City, IA (US)

( * ) Notice: Subject to any disclaimer, the term of this patent is extended or adjusted under 35 U.S.C. 154(b) by 112 days.

(21) Appl. No.: 16/312,705

(22) PCT Filed: Jun. 28, 2017

(86) PCT No.: PCT/US2017/039649
§ 371 (c)(1),
(2) Date: Dec. 21, 2018

(87) PCT Pub. No.: WO2018/005592
PCT Pub. Date: Jan. 4, 2018

(65) Prior Publication Data
US 2019/0388598 A1  Dec. 26, 2019

Related U.S. Application Data

(60) Provisional application No. 62/355,718, filed on Jun. 28, 2016.

(51) Int. Cl.
*A61M 60/894* (2021.01)
*A61M 1/26* (2006.01)
(Continued)

(52) U.S. Cl.
CPC .......... *A61M 60/894* (2021.01); *A61M 1/267* (2014.02); *A61M 1/3666* (2013.01);
(Continued)

(58) Field of Classification Search
CPC .............. A61M 1/1096; A61M 1/1005; A61M 1/1031; A61M 1/1036; A61M 1/122;
(Continued)

(56) References Cited

U.S. PATENT DOCUMENTS

| 1,948,840 A | 2/1934 | Biddle |
| 1,956,101 A | 4/1934 | Le |

(Continued)

FOREIGN PATENT DOCUMENTS

| WO | WO-2018005592 A1 | 1/2018 |
| WO | WO-2018005611 A1 | 1/2018 |

OTHER PUBLICATIONS

"U.S. Appl. No. 16/312,689 Preliminary Amendment Filed Dec. 21, 2018", 9 pgs.

(Continued)

*Primary Examiner* — Christopher A Flory
(74) *Attorney, Agent, or Firm* — Schwegman Lundberg & Woessner, P.A.

(57) ABSTRACT

A medical device includes a constant-flow pump configured to pump a fluid through a fluid conduit and a rotary valve fluidically connected to the pump. The rotary valve includes at least one rotatable valve member configured to be operatively connected to and rotate relative to the fluid conduit. The rotatable valve member includes at least one aperture. The rotatable valve member is capable of being positioned in a plurality of positions relative to the conduit. The position of the at least one first aperture of the rotatable valve member controls fluid flow through the rotary valve, and thereby through the conduit.

27 Claims, 14 Drawing Sheets

(51) Int. Cl.
  *A61M 1/36* (2006.01)
  *A61M 60/148* (2021.01)
  *A61M 60/419* (2021.01)
  *A61M 60/422* (2021.01)
  *A61M 60/562* (2021.01)

(52) U.S. Cl.
  CPC ........ *A61M 60/148* (2021.01); *A61M 60/419* (2021.01); *A61M 60/422* (2021.01); *A61M 60/562* (2021.01)

(58) Field of Classification Search
  CPC .. A61M 1/267; A61M 1/3666; A61M 60/148; A61M 60/267; A61M 60/419; A61M 60/422; A61M 60/562
  See application file for complete search history.

(56) References Cited

U.S. PATENT DOCUMENTS

| | | | |
|---|---|---|---|
| 2,275,477 A | 3/1942 | Sundholm | |
| 3,251,511 A | 5/1966 | Lloyd | |
| 4,174,058 A | 11/1979 | Bassignani | |
| 4,598,697 A * | 7/1986 | Numazawa | A61M 60/562 600/17 |
| 5,054,521 A | 10/1991 | Hendrick | |
| 5,089,016 A | 2/1992 | Millner et al. | |
| 5,178,515 A * | 1/1993 | Tsuchiya | F04D 11/00 415/206 |
| 5,290,227 A * | 3/1994 | Pasque | A61M 60/258 600/16 |
| 5,549,667 A | 8/1996 | Davidson | |
| 5,964,694 A * | 10/1999 | Siess | H02K 49/104 600/17 |
| 6,085,809 A | 7/2000 | Woodruff | |
| 6,264,601 B1 * | 7/2001 | Jassawalla | F04B 43/04 600/16 |
| 6,283,339 B1 | 9/2001 | Morrow | |
| 6,311,674 B1 * | 11/2001 | Igashira | F02M 63/0017 123/458 |
| 6,363,276 B1 * | 3/2002 | Prem | A61M 60/82 607/6 |
| 6,770,024 B1 * | 8/2004 | Rastegar | A61M 1/106 600/16 |
| 6,945,264 B1 | 9/2005 | Denzel et al. | |
| 7,740,026 B2 | 6/2010 | Matsui et al. | |
| 8,672,876 B2 * | 3/2014 | Jacobson | G05D 7/0676 604/67 |
| 8,689,830 B2 | 4/2014 | Chen | |
| 8,720,423 B2 | 5/2014 | Perr et al. | |
| 9,739,395 B2 | 8/2017 | Zimmer et al. | |
| 2002/0094281 A1 * | 7/2002 | Khanwilkar | F04D 13/0666 417/356 |
| 2002/0116054 A1 * | 8/2002 | Lundell | A61F 2/2472 623/2.1 |
| 2003/0023255 A1 * | 1/2003 | Miles | A61M 1/1008 606/158 |
| 2005/0002806 A1 | 1/2005 | Fuechslin et al. | |
| 2005/0016592 A1 | 1/2005 | Jeromson et al. | |
| 2005/0247742 A1 | 11/2005 | Livingston et al. | |
| 2005/0250975 A1 * | 11/2005 | Carrier | F04D 13/0633 600/16 |
| 2006/0016001 A1 | 1/2006 | Zhao | |
| 2006/0278665 A1 | 12/2006 | Bennett et al. | |
| 2008/0249456 A1 * | 10/2008 | Inamori | A61M 60/50 604/6.1 |
| 2009/0112312 A1 * | 4/2009 | LaRose | A61M 1/122 623/3.13 |
| 2010/0268334 A1 * | 10/2010 | Pate | A61M 60/205 623/3.14 |
| 2013/0277119 A1 * | 10/2013 | Rogers | F16F 9/20 175/317 |
| 2013/0287613 A1 * | 10/2013 | Gould | F04B 43/12 417/476 |
| 2013/0343917 A1 * | 12/2013 | Hering | F16K 11/0856 417/53 |
| 2014/0058190 A1 * | 2/2014 | Gohean | A61M 60/258 600/17 |
| 2015/0010415 A1 * | 1/2015 | Yamada | A61M 1/1031 417/420 |
| 2015/0369375 A1 * | 12/2015 | Gattavari | F03B 13/00 137/560 |
| 2016/0045654 A1 * | 2/2016 | Connor | A61M 1/1072 600/17 |
| 2019/0331236 A1 | 10/2019 | Singh et al. | |

OTHER PUBLICATIONS

"International Application Serial No. PCT US2017 039683, International Preliminary Report on Patentability dated Oct. 31, 2019", 8 pgs.
"International Application Serial No. PCT US2017 039649, International Preliminary Report on Patentability dated Oct. 31, 2019", 9 pgs.
"International Application Serial No. PCT/US2017/039649, International Search Report dated Oct. 12, 2017", 5 pgs.
"International Application Serial No. PCT/US2017/039649, Written Opinion dated Oct. 12, 2017", 7 pgs.
"International Application Serial No. PCT/US2017/039683, International Search Report dated Oct. 13, 2017", 5 pgs.
"International Application Serial No. PCT/US2017/039683, Written Opinion dated Oct. 13, 2017", 6 pgs.
Go, Alan, et al., "Heart Disease and Stroke Statistics—2013 Update", Circulation 127.1, (2013), e6-e245.
Slaughter, Mark S., et al., "Advanced heart failure treated with continuous-flow left ventricular assist device", New England Journal of Medicine 361.23, (2009), 2241-2251.
"U.S. Appl. No. 16/312,689, Non Final Office Action dated Oct. 7, 2020", 11 pgs.
"U.S. Appl. No. 16/312,689, Response filed Jul. 28, 2020 to Restriction Requirement dated Apr. 28, 2020", 9 pgs.
"U.S. Appl. No. 16/312,689, Restriction Requirement dated Apr. 28, 2020", 6 pgs.

* cited by examiner

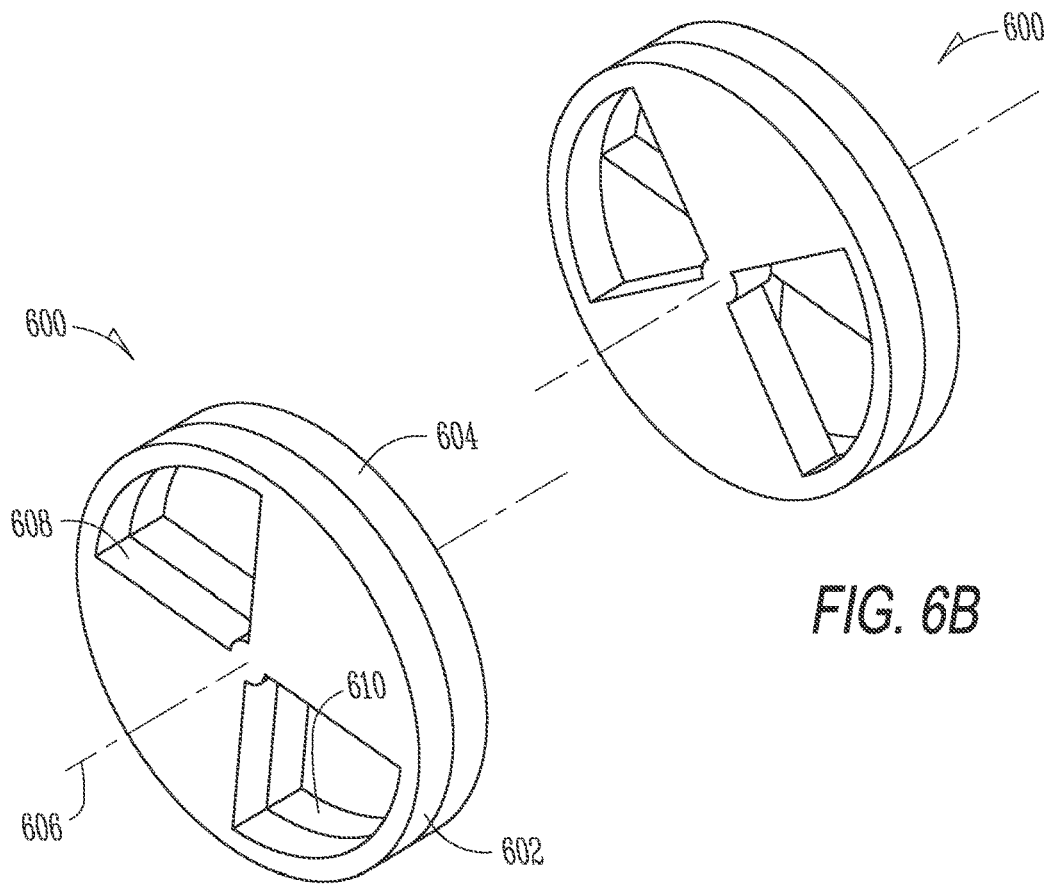
FIG. 6A
FIG. 6B
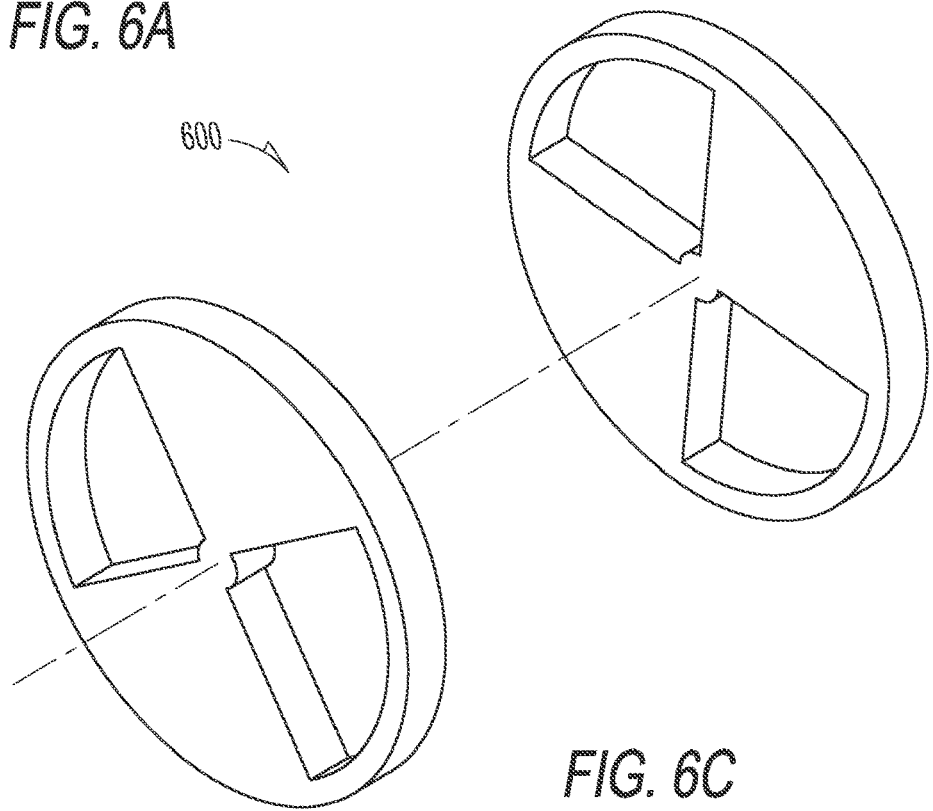
FIG. 6C

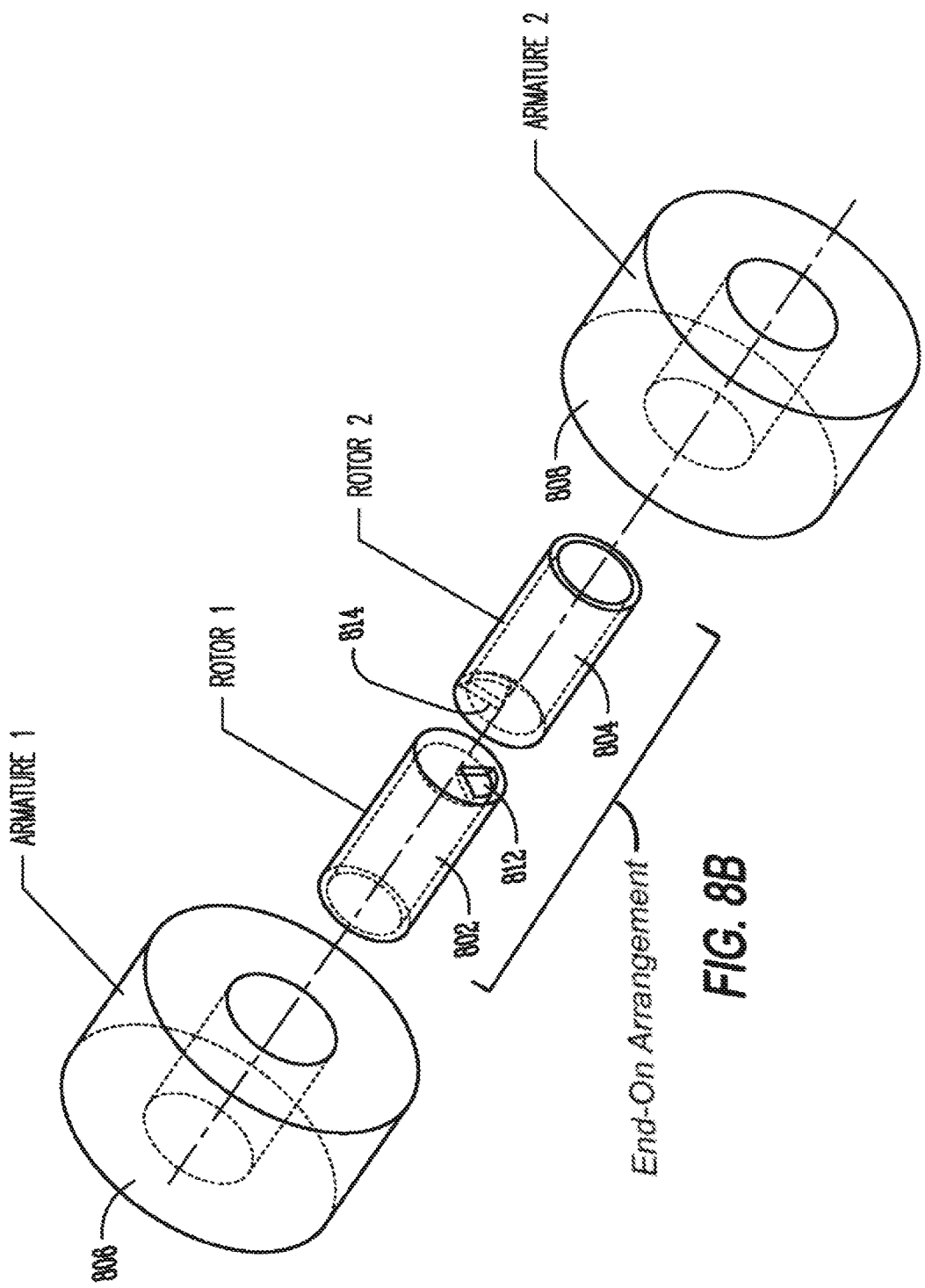

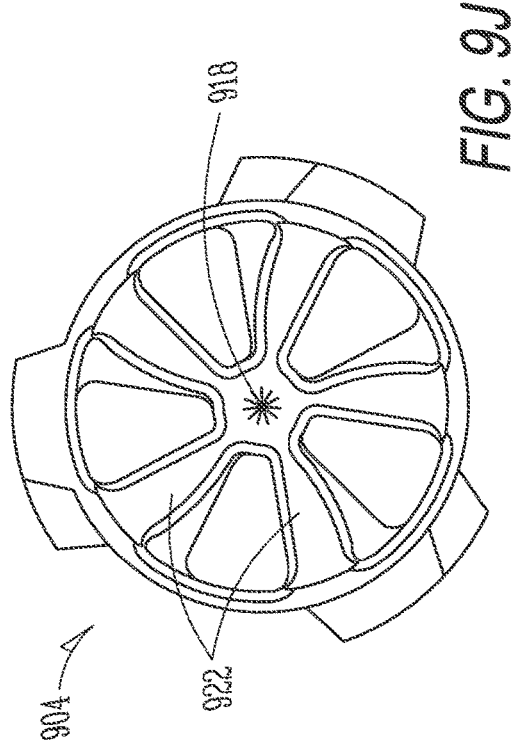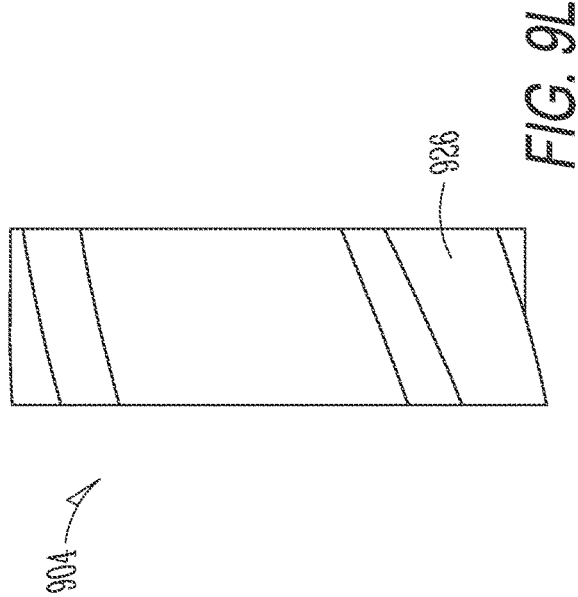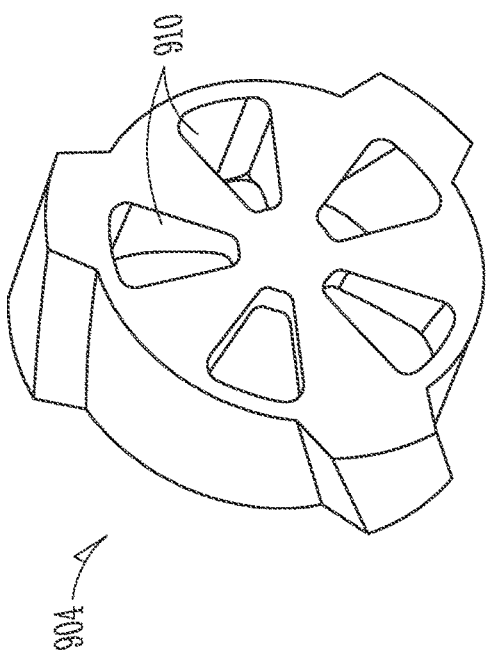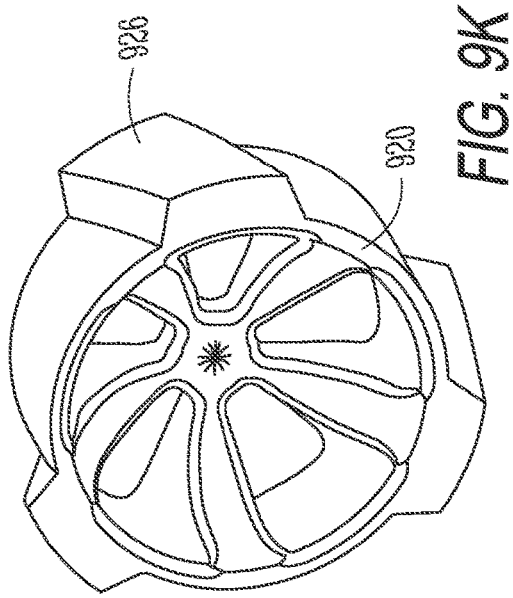

MEDICAL DEVICES INCLUDING ROTARY VALVE

CLAIM OF PRIORITY

This application is a U.S. National Stage Filing under 35 U.S.C. 371 from International Application No. PCT/US2017/039649, filed on Jun. 28, 2017, and published as WO 2018/005592 on Jan. 4, 2018, which application claims the benefit of U.S. Provisional Patent Application Ser. No. 62/355,718, filed on Jun. 28, 2016, the benefit of priority of which are claimed hereby, and which are incorporated by reference herein in their entirety.

DESCRIPTION OF THE DRAWINGS

In the drawings, which are not necessarily drawn to scale, like numerals may describe similar components in different views. Like numerals having different letter suffixes may represent different instances of similar components, sub-components of a larger logical or physical system, or the like. The drawings illustrate generally, by way of example, but not by way of limitation, various examples described in the present disclosure.

FIGS. 6A-6C depict another example valve in accordance with this disclosure.

FIGS. 8A and 8B depict another example rotary valve.

FIGS. 9A-9L depict another example rotary valve in accordance with this disclosure.

DETAILED DESCRIPTION

Figure 1:
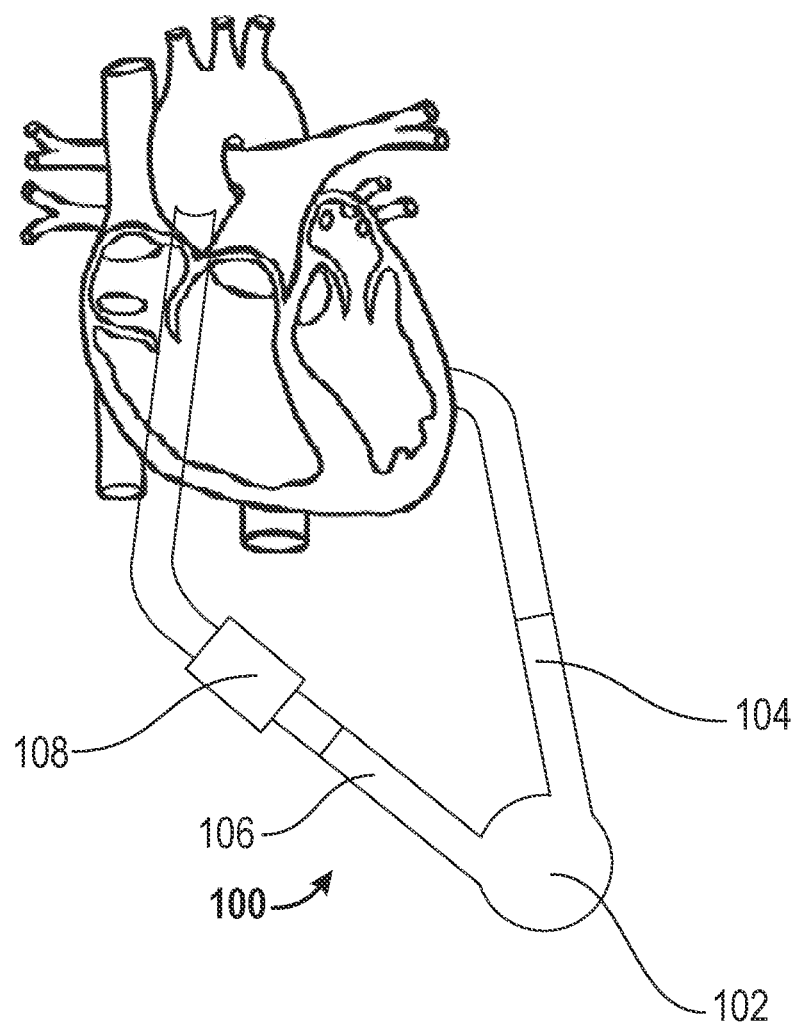
FIG. 1 depicts example LVAD in accordance with this disclosure.

There are a variety of practical applications for which pulsatile or pulsed fluid flow is required or beneficial. Pulsatile flow (PF), as used in this disclosure, is a stream or flow of fluid that flows at other than a substantially constant velocity, volume/mass rate, and/or pressure. There are a number mechanisms by which PF can be produced. For example, a pulsatile fluid pump can be designed to draw fluid from a source and deliver the fluid in a pulsed flow. However, pulsatile pumps tend to be more complex, larger, more challenging to control (if actively controllable at all) and likely more expensive to produce than a constant flow fluid pump.

Examples according to this disclosure are directed to medical devices including a constant-pressure pump and a rotary valve(s), which is capable of delivering pulsatile flow of a fluid at a variety of simply and reliably controlled frequencies, which frequencies can be selected depending upon the intended application. In one example, a rotary valve includes at least one rotatable valve member configured to be operatively connected to and rotate relative to a fluid conduit. The rotatable valve member includes at least one aperture. The rotatable valve member is capable of being positioned in a plurality of positions relative to the conduit. The position of the at least one first aperture of the rotatable valve member controls fluid flow through the rotary valve, and thereby through the conduit. In some cases, a single operational parameter of the valve, angular velocity, can be controlled to deliver a target frequency PF. The valve can rotate continuously or periodically. The valve can rotate in a single or two directions. The valve can also rotate at a constant or variable velocity.

Rotary valves in accordance with this disclosure may be employed to block and let pass fluid flow in a pulsed or constant flow. Additionally, rotary valves in accordance with this disclosure may be employed to control mass/volume flow rate a fluid by varying the cross section of a fluid conduit through which the fluid flows.

As an example application that may benefit from PF, various biological processes in the human body rely on consistent, pulsatile blood flow to be effective. The pressure and velocity of blood flow in the body is controlled by the heart. People who suffer from heart failure require devices to assist in maintaining healthy blood flow. These can be, as examples, a Total Artificial Heart (TAH) or a Ventricular Assist Device (VAD). Research shows CF devices cause problems such as hemolysis, gastrointestinal bleeding, and aortic insufficiency, and cannot be considered as the best possible solutions for patients already suffering from heart failure. Example rotary valves in accordance with this disclosure can capable of producing strong, mathematically accurate PF at required frequencies to mimic the human heart, while being compact and reliable.

5 million Americans currently live with heart failure, and 670,000 new cases are diagnosed each year. Only 2000 advanced heart failure patients receive transplants each year. More than 250,000 advanced heart failure patients have no viable treatment option, and up to 100,000 of these could benefit from a Left Ventricular Assist Device or LVAD. At least some example rotary valves in accordance with this disclosure may make TAH and LVAD systems a long-term solution and a potential alternative for heart transplant surgery.

Example rotary valves in accordance with this disclosure can produce pressure and/or velocity pulses according to a wide variety of mathematical functions (for example, a sine wave). Example valves can be hermetically sealed and can be fitted downstream of a standard axial/centrifugal or other constant flow fluid pump. Simple control logic and easy operation (control of disc speeds) may produce a better response time compared to existing devices delivering PF. The simplicity of the design and operation parameters can increase durability and reliability. Additionally, the valve rotor (and/or stator) design can be optimized to reduce drag and flow separation and generally to reduce and control for fluid pressure loss.

Rotary valves in accordance with this disclosure can be actively or passively actuated. For example, a rotary valve can include one rotor and one stator. At least partially surrounding the rotor can be an electric motor armature and connected to or embedded in the rotor can be a magnetic material. By running a constant or variable electrical current through the armature, the rotor can be rotated continuously or periodically, in one or two directions, to position the rotor in various positions relative to the stator at various constant and/or variable velocities.

In another example, a rotary valve includes two rotors, associated and operatively arranged with each of which is an electric motor armature. Each or both of the armatures can be energized to actuate the rotors to rotate into various positions relative to one another. Simple control of current delivered to the armatures will cause the rotors to rotate at constant or variable angular velocities and thereby deliver simple or complex PF profiles.

Although some examples described herein employ an electrical or electromagnetic actuation mechanism, other types of actuators can be employed to actuate rotary valves in accordance with this disclosure, including, for example, mechanical, electro-mechanical, hydraulic and/or pneumatic actuators. In one example, a rotor of a rotary valve is actuated by a mechanical gear mechanism. For example, the rim or outer periphery of the rotor can include a plurality of gear teeth circumferentially disposed thereabout. A drive gear can be arranged to engage the rotor to actuate the rotor and cause it to rotate at a constant or variable angular velocity.

Additionally, more complex gear mechanisms can be employed to provide increased control and variability to the operation of the valve. For example, the rotor can be operatively connected to a gear box including one or more gears and/or gear trains to provide multiple gear ratios in order to vary the angular velocity of the rotor of the valve.

In another example, a rotary valve is passively actuated. For example, a rotary valve can be arranged at least partially within and operatively connected to a fluid conduit. The rotary valve can include a rotor and a stator. The rotor can be configured to be actuated to rotate relative to the stator by a pressure differential on either side of the valve. Passively actuated valves in accordance to this disclosure can be configured to respond (e.g., actuate) to fluid flow fields applied to them. For example, a rotary valve in accordance with this disclosure can be employed as an artificial heart valve and the blood flow through the passive artificial valve causes the valve to open or close. Another example includes a turbine upstream of an example rotary valve. The turbine can be coupled via a shaft to a rotor of the valve. The fluid flow, in this case, causes the turbine to rotate and, in turn, the turbine rotates the valve.

The PF that can be produced by valves in accordance with this disclosure may have a number of benefits. The pulsivity of the flow may produce certain advantageous flow characteristics, such as advantageous boundary layer effects. Because of the oscillatory behavior of the boundary layer, particle carrying and surface clearing properties may be enhanced.

As noted above, rotary valves in accordance with this disclosure may be employed in a variety of medical applications and to address a number of medical conditions, including, for example, VADs, TAHs, extracorporeal membrane oxygenation (ECMO) machines, dialysis machines, aortic valve function, pulmonary hypertension, cardiopulmonary bypass, renal, liver and/or brain/cognitive function.

CF LVADs may, over time cause a high pressure zone to develop in the aorta, right above the aortic valve. This constant high pressure zone causes damage to the aortic valve flaps so that they're always a little open, causing leakage. Employing a rotary valve in accordance with this disclosure with a CF LVAD may alleviate or reduce this effect and improve aortic valve function.

Pulmonary artery pressure is the pressure the right side of the heart works against: the greater the pressure, the greater the strain on the right side of the heart. This is important for patients with LVADs because these devices assist only the left side of the heart.

Pulmonary artery pressure for healthy human hearts is 20 mmHg (systolic). Research shows that for CF VADs, it can go up to 60 mmHg. Meanwhile, PF VADs can maintain artery pressure at 30 mmHg. This means pulsatile LVADs at least inhibit (relative to CF LVADs) extra strain on the right side of heart by preventing pulmonary hypertension. Low pulmonary artery pressure also means improved lung function. However, as noted above, pulsatile flow pumping devices like pulsatile LVADs can be complicated and costly to produce and may have less longevity than CF devices. Employing a rotary valve in accordance with this disclosure with a CF LVAD may address the issue of pulmonary hypertension in a less costly and complex manner and also make such devices more affordable and longer lasting.

Cardiopulmonary bypass, which is also known as a heart-lung machine is used to support the body during a surgical procedure during which the heart has to be stopped. Such devices may use a roller pump or centrifugal pump to move the blood, but it is typically a continuous flow pump. Patients spend a limited amount of time on such machines, for example 2-4 hours, but this may be enough time to cause organ damage due to lack of pulsatility. Arranging a rotary valve in accordance with this disclosure downstream of a pump on such a device will produce programmable pulsatility, and can thereby reduce such damage.

An extracorporeal membrane oxygenation (ECMO) machine acts as a heart pump as well as an artificial lung (oxygenator). Such devices also may use CF roller pumps. Patients can however spend more time on ECMO devices, comparatively, for example, on the order of a week. Rotary valves in accordance with this disclosure may be employed to prevent or reduce organ damage or other deleterious effects.

Dialysis machines use diffusive mass transport in membranes to clean blood, and roller pumps to move the blood. The PF produced by rotary valves in accordance with this disclosure can enhance mass transport, making the machines lighter, smaller and more easily transportable.

Although many implantable LVADs, RVADs, and TAHs produce PF, such devices can be complex, costly and exhibit reduced durability and longevity relative to such a device with a simple CF pump and not additional PF mechanism. Thus such devices may benefit from incorporation of a rotary valve in accordance with this disclosure. Additionally, temporary VADs (left and right) are directed to a similar function as implantable devices but typically employ a CF pump and are meant only as a temporary solution for patients. In practice, however, patients can spend months on such devices while they await heart transplant or LVAD implant surgery and such devices could therefore benefit from the PF produced by a rotary valve in accordance with this disclosure.

Moreover, current designs of TAHs are relatively complicated machines, which use pneumatic actuation to produce pulsation. The resulting setup can be mechanically complicated and heavy. Such a TAH may be replaced with two CF LVADs and two valves in accordance with this disclosure, and the setup would become considerably less unwieldy as well as mechanically simpler, not to mention possibly less expensive, more durable and longer lasting.

FIG. 1 depicts example LVAD 100 in accordance with this disclosure. LVAD 100 includes pump 102, fluid conduits 104 and 106, and rotary valve 108. LVAD is configured to be coupled to the heart of a patient to replace/augment/correct function of the left side of the heart by drawing blood from the left ventricle and delivering the blood to the aorta. Pump 102 is a constant-flow pump, which means that the pump is configured to continuously transport/pump fluid there through versus oscillating pumping or flow to deliver a pulsed or pulsatile flow (PF). Pump 102 is coupled on the inlet side to fluid conduit 104, for example, a catheter, which is coupled to the left ventricle of the heart. Pump 102 is coupled on the outlet side to fluid conduit 106, for example, a catheter, which is coupled to the aorta.

Example rotary valve 108 in accordance with this disclosure is arranged between the outlet of pump 102 and the aorta and operatively coupled to fluid conduit 106. In one example, rotary valve 108 includes at least one rotatable valve member configured to be operatively connected to and rotate relative to fluid conduit 106. The rotatable valve member includes at least one aperture. The rotatable valve member is capable of being positioned in a plurality of positions relative to conduit 106. The position of the at least one first aperture of the rotatable valve member controls blood flow through rotary valve 108, and thereby through conduit 106. In some cases, a single operational parameter of the valve, angular velocity, can be controlled to deliver a target frequency PF. The valve can rotate continuously or periodically. The valve can rotate in a single or two directions. The valve can also rotate at a constant or variable velocity. Rotary valve 108 can be controlled to deliver PF that mimics/estimates blood flow produced naturally by the heart.

LVAD 100 can be an external or implantable medical device. Additionally, LVAD 100 may be employed by patients on a temporary basis, or, in other words, for relatively limited periods of times, in which case, LVAD 100 may be an external device connected to the patients hear via catheters (fluid conduits 104 and 106) percutaneously. In other cases, LVAD 100 may be employed by patients on a semi-permanent basis, or in other words, for relatively longer periods of times, in which case, pump 102, conduits 104 and 106 and valve 108 may be implanted and the pump may be percutaneously coupled to a power source and controller.

Although example valve 108 has been depicted and described in association with LVAD 100, rotary valves in accordance with this disclosure can also be employed with an RVAD, as well as other medical devices, including the examples described below with reference to FIGS. 2-4.

Figure 2:
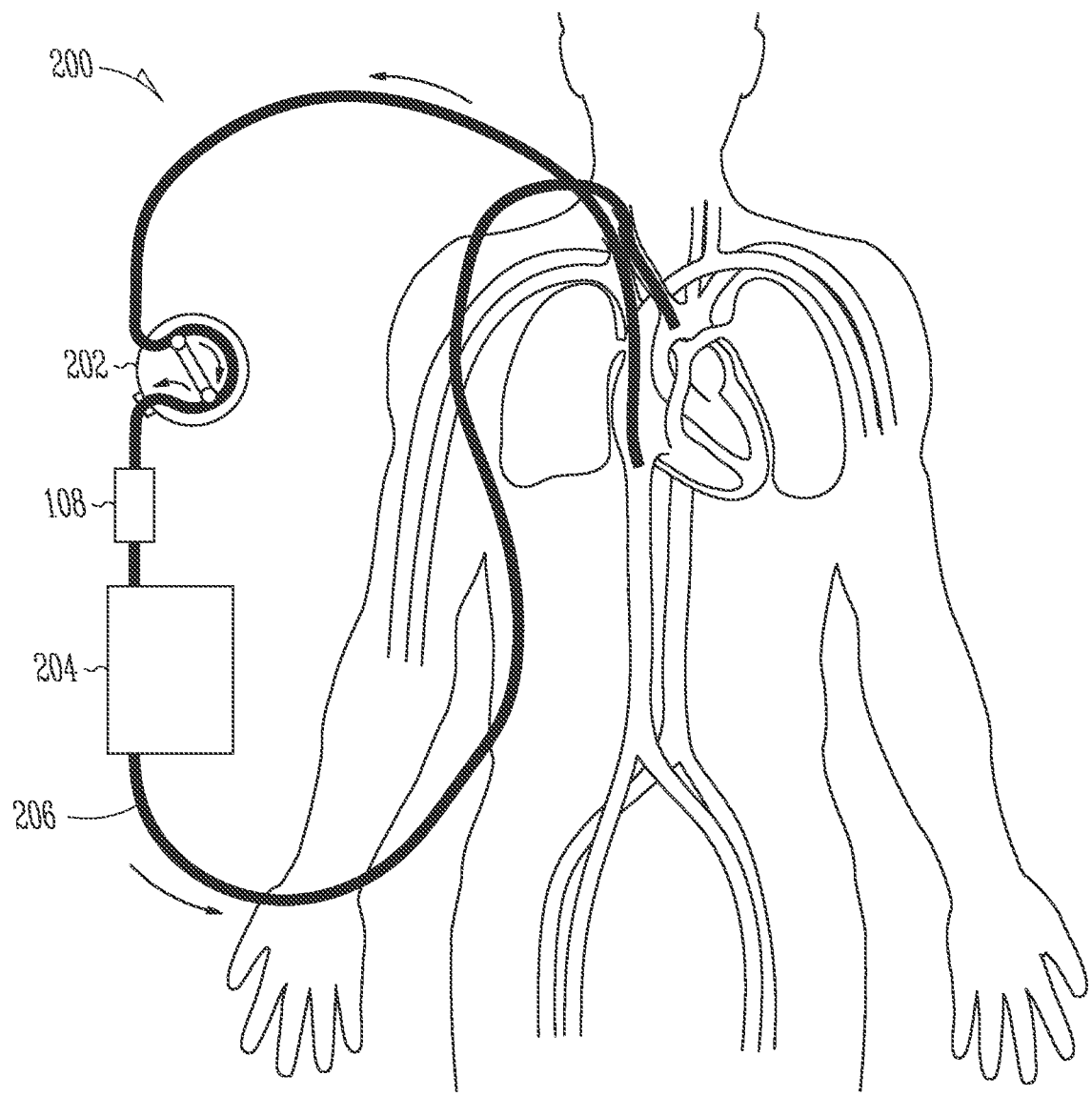
FIG. 2 depicts example ECMO device in accordance with this disclosure.

FIG. 2 depicts example ECMO device 200 in accordance with this disclosure. Extracorporeal membrane oxygenation (ECMO), also known as extracorporeal life support (ECLS), is an extracorporeal technique of providing both cardiac and respiratory support to persons whose heart and lungs are unable to provide an adequate amount of gas exchange to sustain life. ECMO works by removing blood from the person's body and artificially removing the carbon dioxide and oxygenating red blood cells. Cardiopulmonary bypass (employing a device sometimes referred to as a "heart-lung" machine") is generally used for shorter-term treatment.

ECMO device 200 includes pump 202, artificial lung 204, conduit 206 and example rotary valve 108. Pump 202 and artificial lung 204 are connected to one another and the body of a patient by conduit 206, including, e.g., a catheter or cannula connected to artery/vein percutaneously. Rotary valve 108 is disposed between pump 202 and artificial lung 204 and is operatively connected to conduit 206.

Pump 202 is a constant-flow pump. However, rotary valve 108 can be controlled to deliver PF of blood that is pumped continuously by pump 202. For example, rotary valve 108 can be controlled to deliver PF that mimics/estimates blood flow produced naturally by the heart. The PF delivered by valve 108 can aid in issues associated with CF pumping of blood into patients, and, also may improve the efficiency and overall function of artificial lung 204 by, for example, improving mass transfer.

In operation, pump 202 draws deoxygenated blood from the body via conduit 206 and pumps the blood in a continuous/constant flow tow artificial lung 204. Rotary valve 108 is disposed between pump 202 and lung 204 and receives the CF blood from the pump and delivers PF flow to and through lung 204, and after that the PF blood, from which carbon dioxide has been removed and to which oxygen has been added by lung 204, flows back into the body.

Figure 3:
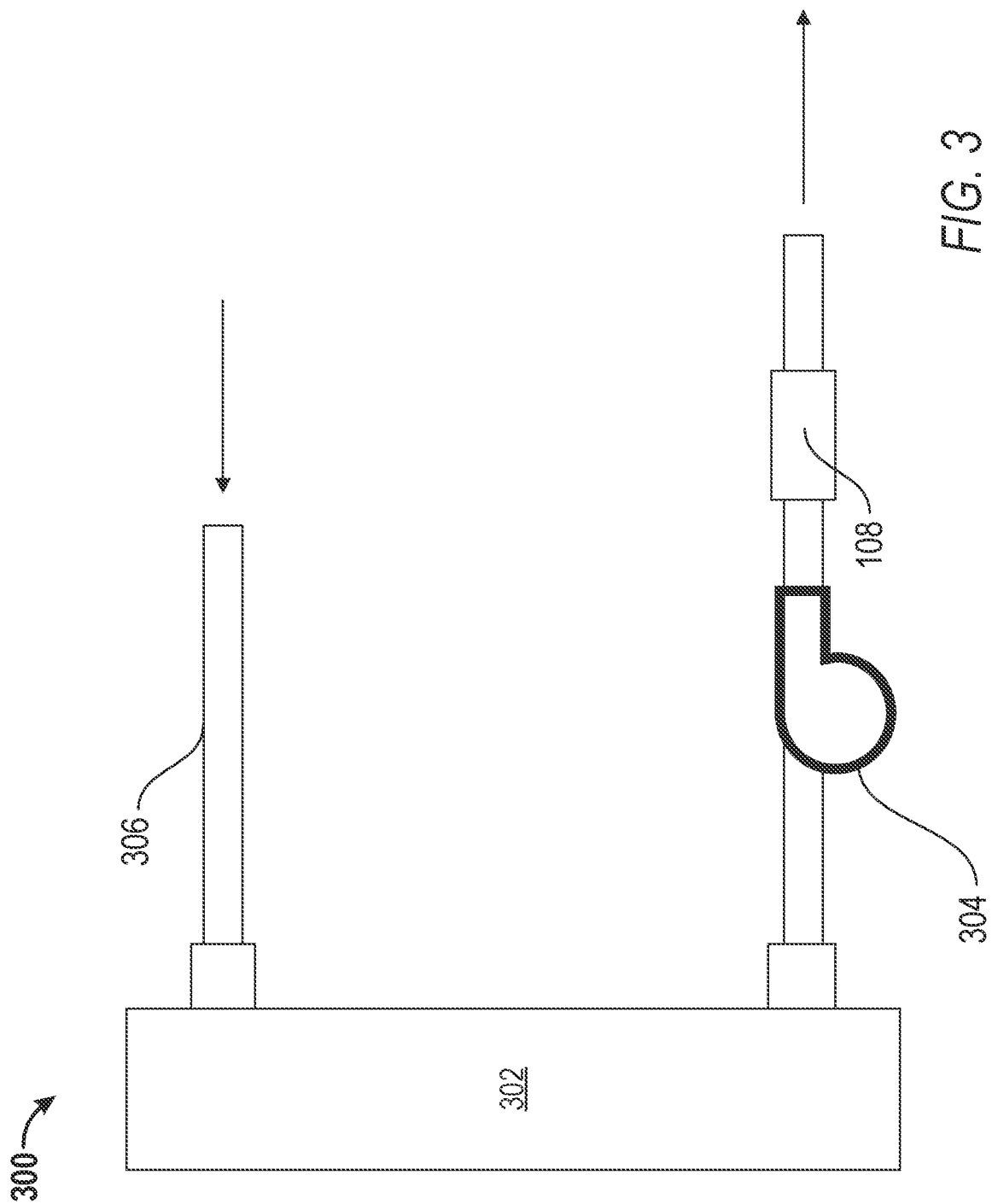
FIG. 3 depicts example dialysis device in accordance with this disclosure.

FIG. 3 depicts example dialysis device 300 in accordance with this disclosure. Dialysis device 300 includes dialyser 302, pump 304, conduit 306 and example rotary valve 108. Dialysis device 300 is configured to remove waste and excess water from the blood and may be used as an artificial replacement for lost kidney function. The kidneys have an important role in maintaining health by maintaining an internal equilibrium of water and minerals in the blood. The acidic metabolism end-products that the body cannot get rid of via respiration are also excreted through the kidneys. The kidneys also function as a part of the endocrine system, producing erythropoietin, calcitriol and renin. Dialysis device 300 may be configured to replace some of these functions through diffusion (waste removal) and ultrafiltration (fluid removal). Dialysis device 300 may use highly purified (also known as "ultrapure") water to accomplish some of these functions.

The diffusion and filtration functions of dialysis device 300 are generally carried out by dialyser 302. Dialyser 302 may be configured to diffuse and filter blood across a semipermeable membrane with the blood flowing on one side of the membrane and a dialysate, or special dialysis fluid, flowing by the opposite side.

Pump 304 is a constant-flow pump. However, rotary valve 108 can be controlled to deliver PF of blood that is pumped continuously by pump 304. For example, rotary valve 108 can be controlled to deliver PF that mimics/estimates blood flow produced naturally by the heart. The PF delivered by valve 108 can aid in issues associated with CF pumping of blood into patients, and, also may improve the efficiency and overall function of dialyser 302 by, for example, improving mass transfer across the semipermeable membrane thereof.

In operation, pump 304 draws blood from the body via conduit 306 and pumps the blood in a continuous/constant flow toward dialyser 302. Rotary valve 108 is disposed between pump 304 and dialyser 302 and receives the CF blood from the pump and delivers PF flow to and through dialyser 302, and after that the PF blood flows back into the body.

Figure 4:
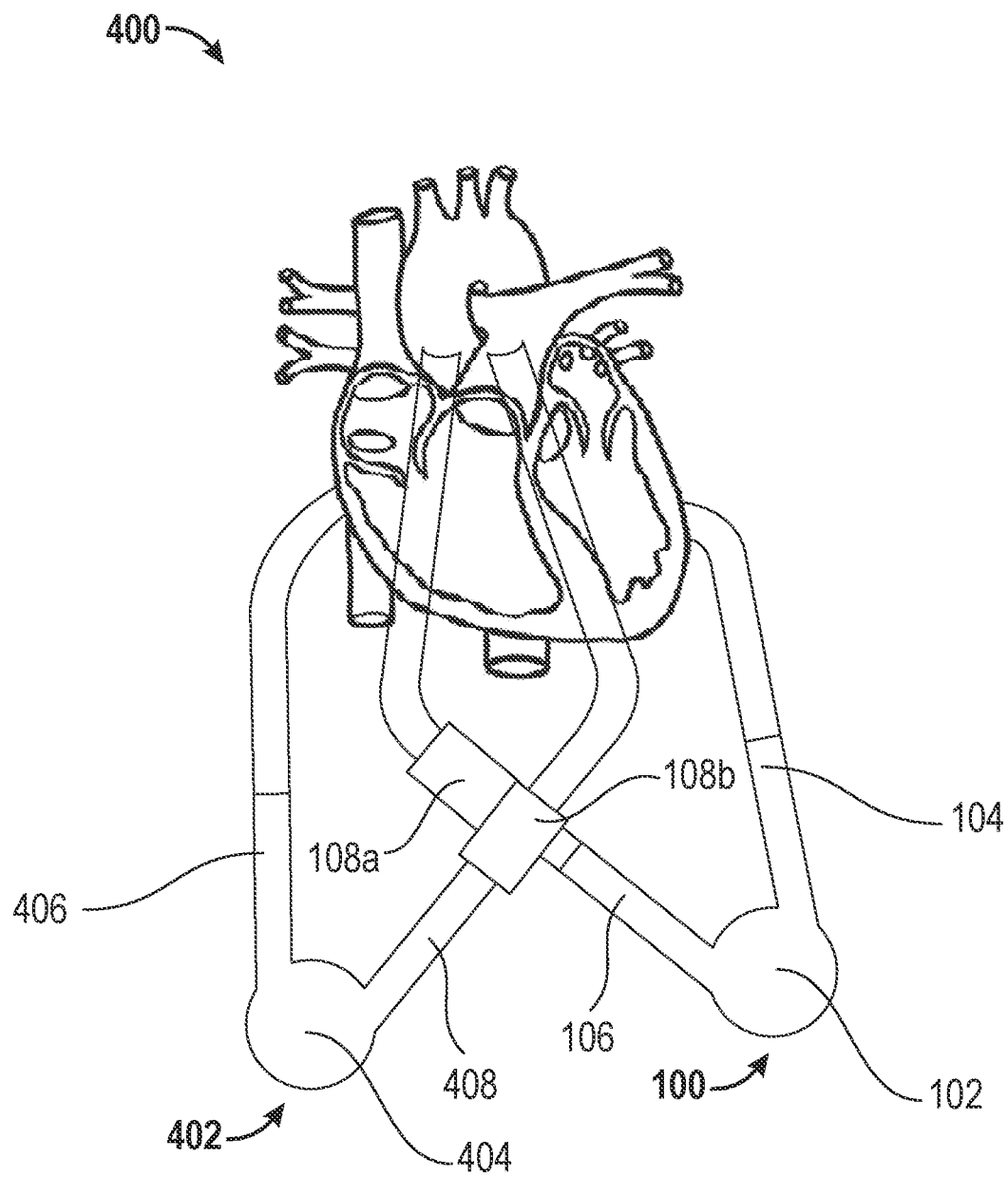
FIG. 4 depicts example medical device in accordance with this disclosure.

FIG. 4 depicts example medical device 400 in accordance with this disclosure. Device 400 includes LVAD 100, including pump 102, fluid conduits 104 and 106, and rotary valve 108. Medical device 400 also includes RVAD 402, including pump 404, conduits 404 and 406, and a second example rotary valve 108. The combination of LVAD 100, RVAD 402, and rotary valves in accordance with this disclosure may function as a Total Artificial Heart (TAH) device.

LVAD 100 is configured to be coupled to the heart of a patient to replace/augment/correct function of the left side of the heart by drawing blood from the left ventricle and delivering the blood to the aorta. Pump 102 is a constant-flow pump, which means that the pump is configured to continuously transport/pump fluid there through versus oscillating pumping or flow to deliver a pulsed or pulsatile flow (PF). Pump 102 is coupled on the inlet side to fluid conduit 104, for example, a catheter, which is coupled to the left ventricle of the heart. Pump 102 is coupled on the outlet side to fluid conduit 106, for example, a catheter, which is coupled to the aorta.

RVAD 402 is configured to be coupled to the heart of a patient to replace/augment/correct function of the right side of the heart by drawing blood from the right ventricle and delivering the blood to the pulmonary artery. Pump 404 is a constant-flow pump, which means that the pump is configured to continuously transport/pump fluid there through versus oscillating pumping or flow to deliver a pulsed or pulsatile flow (PF). Pump 404 is coupled on the inlet side to fluid conduit 406, for example, a catheter, which is coupled to the right ventricle of the heart. Pump 404 is coupled on the outlet side to fluid conduit 408, for example, a catheter, which is coupled to the pulmonary artery.

The first example rotary valve 108a in accordance with this disclosure is arranged between the outlet of pump 102 and the aorta and operatively coupled to fluid conduit 106. The second example rotary valve 108b is arranged between the outlet of pump 404 and the pulmonary artery and operatively coupled to fluid conduit 408. In one example, each of rotary valves 108a and 108b includes at least one rotatable valve member configured to be operatively connected to and rotate relative to fluid conduit 106. The rotatable valve member includes at least one aperture. The rotatable valve member is capable of being positioned in a plurality of positions relative to conduits 106 and 408. The position of the at least one first aperture of the rotatable valve member controls blood flow through the rotary valve, and thereby through the conduit. Rotary valves 108a and 108b can be controlled to deliver PF that mimics/estimates blood flow produced naturally by a functioning heart.

Figure 5:
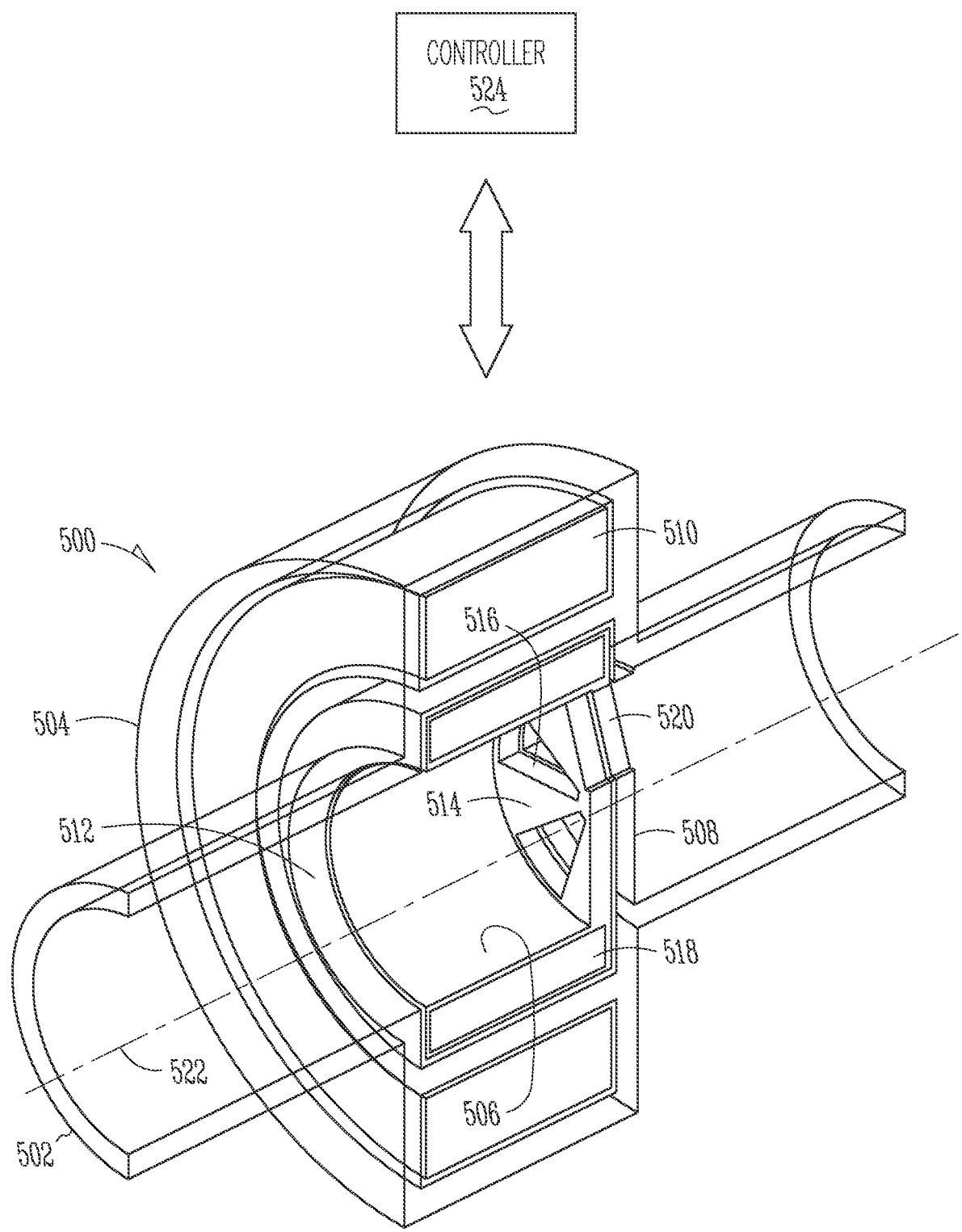
FIG. 5 depicts an example rotary valve in accordance with this disclosure.

FIG. 5 depicts an example rotary valve 500 in accordance with this disclosure. Rotary valve 500 (and other examples described below) may be employed in various applications, including the medical applications described herein. In addition to the example valves described herein, additional example rotary valves are disclosed and described in PCT App. No. PCT/US2017/039683, filed on Jun. 28, 2017, entitled "ROTARY VALVE," the entire contents of which are incorporated herein by reference.

In FIG. 5, valve 500 is operatively coupled to fluid conduit 502. Valve 500 includes housing 504, rotor 506, stator 508, and armature 150. Housing 504 holds rotor 506 and armature 510. Stator 508 is coupled to or integral with housing 504. In another example, stator 508 can be coupled to or integral with conduit 502. In some examples, housing 504 and/or rotary valve 500 may include seal mechanisms, including being hermetically sealed. Forming rotary valve 500 (or another example valve in accordance with this disclosure) as a hermetically sealed device may be particular advantageous or required for certain applications, including, e.g., biomedical applications.

Housing 504 is cylindrical and sized and shaped to receive armature 510 and rotor 506, which is nested within armature 510 inside housing 504. Housing 504 can be coupled to conduit 502 using various coupling mechanisms and/or fasteners. Additionally, a valve housing and fluid conduit can be integral with one another.

Rotor 506 is an annular, in this example cylindrical tubular member with open end 512 and partially closed end 514. Partially closed end 514 of rotor 506 is formed as a disc including a number of apertures 516. In other examples, rotor 506 can include more or fewer apertures 516. For example, rotor 506 can include one aperture or more than four apertures 516. In the example of FIG. 5, apertures 516 in rotor 506 are triangular or pie shaped. However, in other examples, rotor 506 can include differently shaped apertures or other openings such as slots, notches, cutouts, as examples.

Rotor 506 also includes magnetic core 518. Magnetic core 518 can be a separate component coupled to rotor 506 or can be formed integral therewith. Additionally, rotor 506 can be formed in whole or in part of a magnetic material that functions as magnetic core 518. In one example, magnetic core 518 is a permanent magnet.

Stator 508 is formed as a disc including a number of apertures 520. In other examples, stator 508 can include more or fewer apertures 520. For example, stator 508 can include one aperture or more than four apertures 520. In the example of FIG. 5, apertures 520 in stator 508 are triangular or pie shaped. However, in other examples, stator 508 can include differently shaped apertures or other openings such as slots, notches, cutouts, as examples.

Rotor 506 and stator 508 are disposed adjacent one another within valve 500 and conduit 502. Rotor 506 is configured to rotate about axis 522, which is, in this example, also the longitudinal axis of conduit 502. Stator 508 is configured to remain stationary and is aligned centrally with axis 522.

Rotary valve 500 is configured to be actively actuated by armature 510. For example, Armature 510 can include an electrical conductive member configured to convey electrical energy from a power source. Armature 510 is disposed around rotor 506, which includes magnetic core 518. By running a constant or variable electrical current through armature 510, rotor 506 can be rotated continuously or periodically, in one or two directions, to position the rotor in various positions relative to stator 506 at various constant and/or variable velocities.

For example, rotor 506 can be actuated by armature 510 to rotate at a constant angular velocity. The angular velocity of rotor 506 can be selected to produce a target frequency pulsatile flow through conduit 502, given the number and size of apertures 516 and 520 in rotor 506 and stator 508, respectively. As apertures 516 in rotor 506 rotate into alignment with apertures 520 in stator 508, fluid can flow through valve 500 and conduit 502. As apertures 516 in rotor 506 rotate out of alignment with apertures 520 in stator 508, fluid flow through valve 500 and conduit 502 is stopped.

In another example, rotor 506 can be actuated by armature 510 to rotate at a variable angular velocity. For example, rotor 506 can be actuated to rotate at a first angular velocity when apertures 516 in rotor 506 are partially or completely aligned with apertures 520 in stator 506 and at a second, different angular velocity when apertures 516 in rotor 506 are partially or completely unaligned with apertures 520.

In another example, rotor 506 can be actuated by armature 510 to rotate to a particular position relative to stator 508 at a first time and can be actuated by armature 510 to rotate into a second position relative to stator 508 at a second time. The position of rotor 506 relative to stator 508, and, in particular, the position of apertures 516 relative to apertures 520 can effectively change the cross-section of conduit 502, thereby changing the mass/volume flow rate through valve 500. In this manner, rotary valve 500 may be employed to control mass/volume flow rate by varying the flow cross section of fluid conduit 502.

Although rotary valve 500 employs electrical/electromagnetic actuation mechanism, other types of actuators can be employed to actuate rotary valves in accordance with this disclosure, including, for example, mechanical, electro-mechanical, hydraulic and/or pneumatic actuators. For example, rotor 506 of rotary valve 500 can be actuated by a mechanical gear mechanism. The rim or outer periphery of rotor 506 can include gear teeth circumferentially disposed thereabout. A drive gear (or multiple gears) can be arranged to engage rotor 506 to actuate the rotor and cause it to rotate at a constant or variable angular velocity.

Actuation and operation of rotary valve 500 (and other example rotary valves in accordance with this disclosure) can be controlled in a variety of ways. In FIG. 5, rotary valve and armature 510 thereof are communicatively connected to controller 524. Controller 524 can include hardware, software, and combinations thereof to implement the functions attributed to the controller herein. Controller 524 can be an analog, digital, or combination analog and digital controller including a number of components. As examples, controller 524 can include ICB(s), PCB(s), processor(s), data storage devices, switches, relays, etcetera. Examples of processors can include any one or more of a microprocessor, a controller, a digital signal processor (DSP), an application specific integrated circuit (ASIC), a field-programmable gate array (FPGA), or equivalent discrete or integrated logic circuitry.

Storage devices, in some examples, are described as a computer-readable storage medium. In some examples, storage devices include a temporary memory, meaning that a primary purpose of one or more storage devices is not long-term storage. Storage devices are, in some examples, described as a volatile memory, meaning that storage devices do not maintain stored contents when the computer is turned off. Examples of volatile memories include random access memories (RAM), dynamic random access memories (DRAM), static random access memories (SRAM), and other forms of volatile memories known in the art. The data storage devices can be used to store program instructions for execution by processor(s) of controller 524. The storage devices, for example, are used by software, applications, algorithms, as examples, running on and/or executed by controller 524. The storage devices can include short-term and/or long-term memory, and can be volatile and/or non-volatile. Examples of non-volatile storage elements include magnetic hard discs, optical discs, floppy discs, flash memories, or forms of electrically programmable memories (EPROM) or electrically erasable and programmable (EE-PROM) memories.

Controller 524 can be configured to communicate with and/or directly control a power source (and associated circuitry) providing power to armature 510 of rotary valve 500. Controller 524 can be configured to communicate via various wired or wireless communications technologies and components using various public and/or proprietary standards and/or protocols. For example, a power and/or communications network of some kind may be employed to facilitate communication and control between controller 524 and rotary valve 500 (or a larger system in which the valve is employed). In one example, controller 524 may communicate via a private or public local area network (LAN), which can include wired and/or wireless elements functioning in accordance with one or more standards and/or via one or more transport mediums. In one example, controller 524 can be configured to use wireless communications according to one of the 802.11 or Bluetooth specification sets, or another standard or proprietary wireless communication protocol. Data transmitted to and from controller 524, can be formatted in accordance with a variety of different communications protocols. For example, all or a portion of the communications can be via a packet-based, Internet Protocol (IP) network that communicates data in Transmission Control Protocol/Internet Protocol (TCP/IP) packets, over, for example, Category 5, Ethernet cables or over an 802.11 or Bluetooth wireless connection.

Controller 524 can include one or more programs, circuits, algorithms or other mechanisms for controlling the operation of rotary valve 500. For example, controller 524 can be configured to modulate the speed of rotary valve 500 to produce a target PF frequency through the valve. In accordance with relatively simple programming or configuration of controller 524, rotary valve 500 can produce pressure and/or velocity fluid pulses according to a wide variety of mathematical functions.

Rotary valve 500 and other example valves in accordance with this disclosure can be fabricated using a variety of manufacturing and production methods and techniques. Additionally, valve 500 (and other example valves) can be formed of a variety of materials depending, at least in part, on the intended application. As examples, rotary valve 500 and components thereof can be fabricated from various plastics, metals, and/or ceramics. In some applications, valve 500 may be formed of non-corrosive and/or biocompatible materials.

FIGS. 6A-6C depict another example valve 600 in accordance with this disclosure. Valve 600 is depicted in a simplified manner without being arranged within a particular fluid conduit or without depicting a particular actuation mechanism. However, valve 600 and other example valves described below can be disposed with respect to a conduit, actuated, and controlled in a manner consistent with that described above with reference to the example of valve 500 of FIG. 5 with the appropriate modifications for the particular example valve and intended application thereof. In the case of valve 600, for example, the valve can be arranged within or along a fluid conduit with a flow passage approximately sized to the outer diameter of valve 100 and can be actuated by one or more electrical armatures or other actuation mechanisms.

In FIGS. 6A-6C, rotary valve 600 includes two parallel discs, 602 and 604, at least one of which is rotatable about axis 606. As explained, discs 602 and 604 are configured to be operatively coupled to and arranged at least partially within a fluid conduit. Disc 602 includes two apertures 608. Disc 604 includes two apertures 610. Apertures 608 and 610 in discs 602 and 604, respectively, are triangular or pie shaped. However, in other examples, discs 602 and 604 can include differently shaped apertures or other openings such as slots, notches, cutouts, as examples. Additionally, each of discs 602 and 604 can include more or fewer than two apertures. By controlling the shape of apertures 608 and 610 and the angular velocity of one or both of discs 602 and 604 it is possible to attain fluid flows that fit virtually any desired velocity or pressure field. In some cases, both discs 602 and 604 rotate. In another example, one of discs 602 and 604 is a rotor and the other a stator.

Valve 600 can be actuated to rotate one or both of discs 602 and 604 at a constant or variable angular velocity, and one or both of discs 602 and 604 in one or multiple directions. The angular velocity of the rotating valve members of valve 600, whether one or both of discs 602 and 604, can be selected to produce a target frequency pulsatile flow through a conduit. As apertures 608 in disc 602 rotate into alignment with apertures 610 in disc 604, fluid can flow through valve 600 and a fluid conduit to which the valve is operatively coupled. As apertures 608 in disc 602 rotate out of alignment with apertures 610 in disc 604, fluid flow through valve 600 is stopped.

Figure 7:
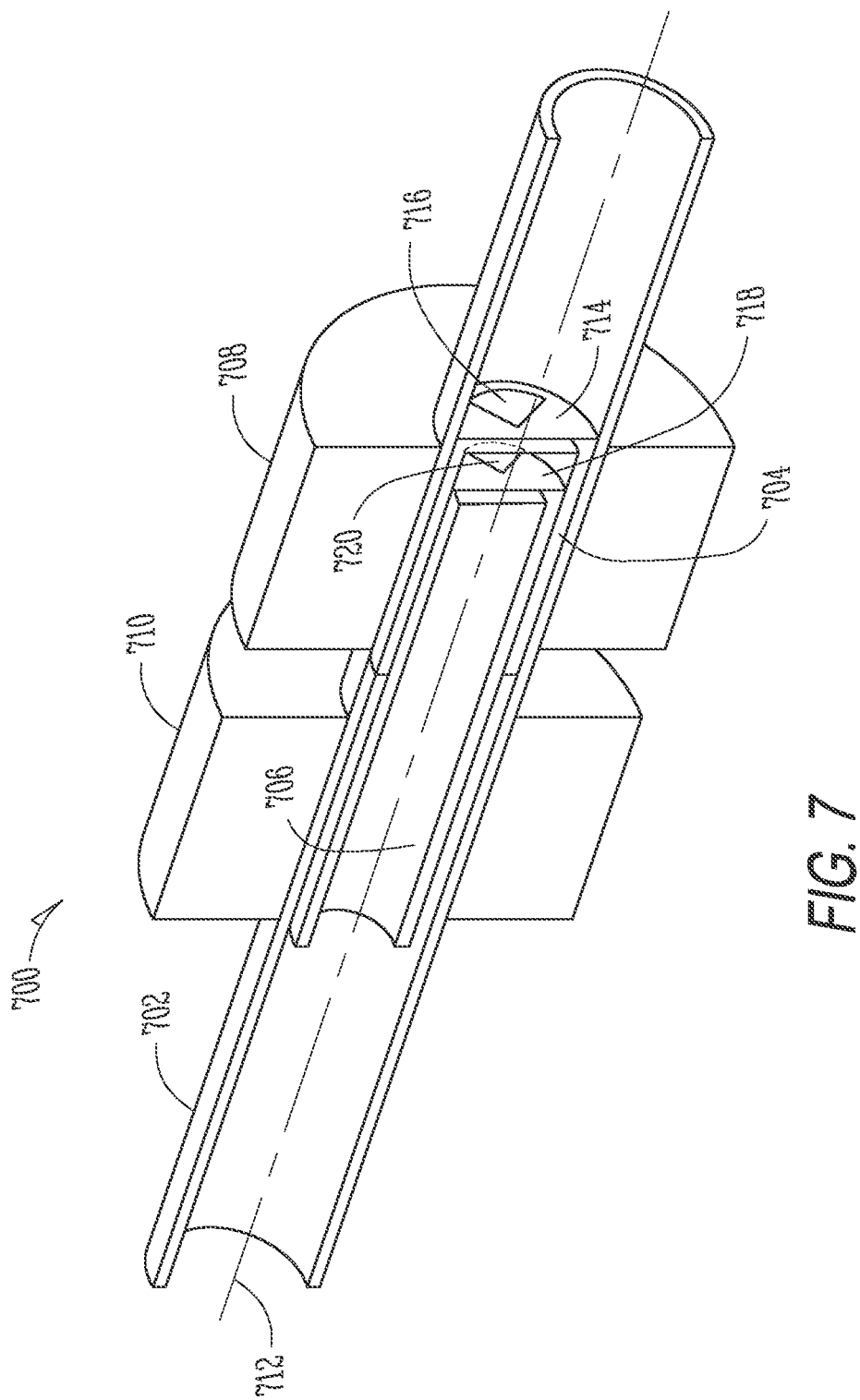
FIG. 7 depicts another example rotary valve.

FIG. 7 is a section view depicting another example rotary valve 700 in accordance with this disclosure. In FIG. 7, valve 700 is operatively coupled to fluid conduit 702. Valve 700 includes outer rotor 704, inner rotor 706, outer rotor armature 708 and inner rotor armature 710. Valve 700 is configured to be actuated by one or both of armatures 708 and 710 to rotate one or both of rotors 704 and 706 about axis 712 (axis of rotation of rotors/valve and longitudinal axis of conduit) to control flow of a fluid through conduit 702.

Outer rotor 704 and inner rotor 706 are what may be referred to as nested tubular rotors. Outer rotor 704 is an annular, in this example cylindrical tubular member with an open end and partially closed end 714. Partially closed end 714 of rotor 704 is formed as a disc including an aperture 716. Inner rotor 706 is also an annular, in this example cylindrical tubular member with an open end and partially closed end 718. Partially closed end 718 of rotor 706 is formed as a disc including an aperture 720. In other examples, one or both of rotors 704 and 706 can include more than one aperture. In the example of FIG. 1, apertures 716 and 720 are triangular or pie shaped. However, in other examples, rotors 704 and 706 can include differently shaped apertures or other openings such as slots, notches, cutouts, as examples.

Inner rotor 706 is nested or received in outer rotor 704. FIG. 7 depicts ends 714 and 718 of outer rotor 704 and inner rotor 706 as offset, but this is at least in part to illustrate the structure of each rotor. In operation, partially ends 714 and 718 of outer rotor 704 and inner rotor 706 including apertures 716 and 720 may abut one another so that the closed end of the inner rotor is pushed up against the closed end of the outer rotor. Inner rotor 706 extends beyond and is longer than outer rotor 704 and the nested outer and inner rotors of example rotary valve 700 are disposed in and along the flow path of fluid conduit 702.

Each of rotors 704 and 706 include a magnetic core are formed at least in part from a magnetic material. Magnetic cores of rotors 704 and 706 can be a separate component coupled to each rotor or can be formed integral therewith.

Rotary valve 700 is configured to be actively actuated by one or both of armatures 708 and 710 being energized to rotate one or both of outer rotor 704 and inner rotor 706. As with other example valves in accordance with this disclosure, each of rotors 704 and 706 can be controllably actuated to rotate in one or two directions and at a constant or variable angular velocity. Additionally, each of rotors 704 and 706 can rotate at the same speed in the same directions or at different speeds in different directions, or at the same speeds in different directions or at different speeds in the same direction.

The angular velocity of rotors 704 and 706 can be selected to produce a target frequency pulsatile flow through conduit 702, given the number and size of apertures 716 and 720. As aperture 716 in rotor 704 rotates into alignment with aperture 720 in rotor 706, fluid can flow through valve 700 and conduit 702. As aperture 716 in rotor 704 rotates out of alignment with aperture 720 in rotor 706, fluid flow through valve 700 and conduit 702 is stopped.

Figure 8A:
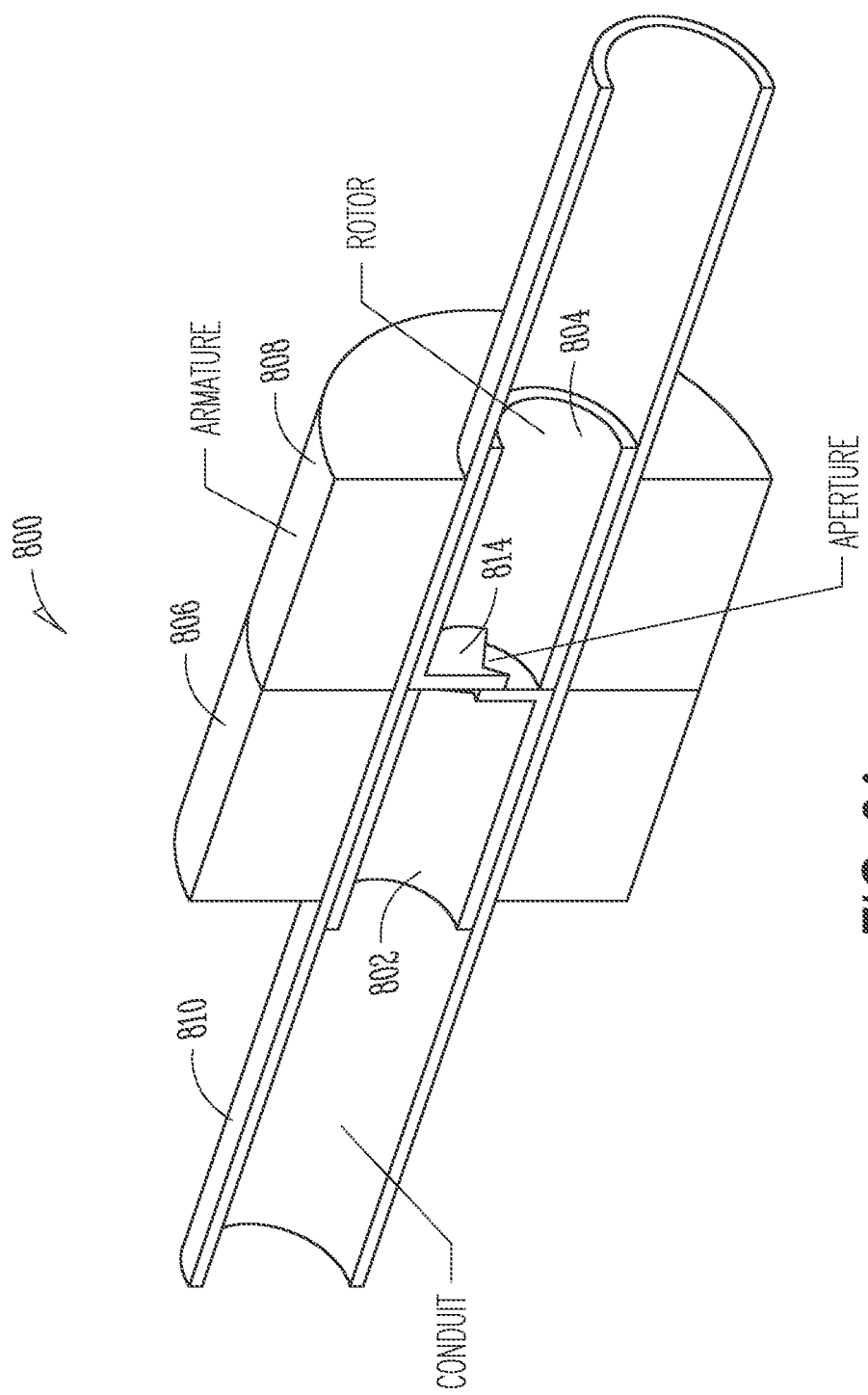
Figure 9B:
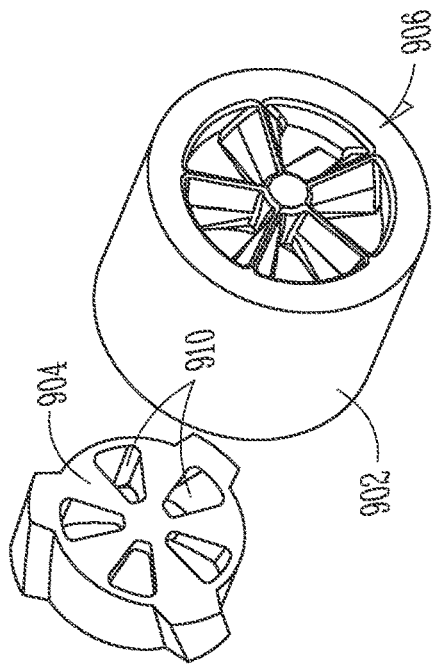
Figure 9D:
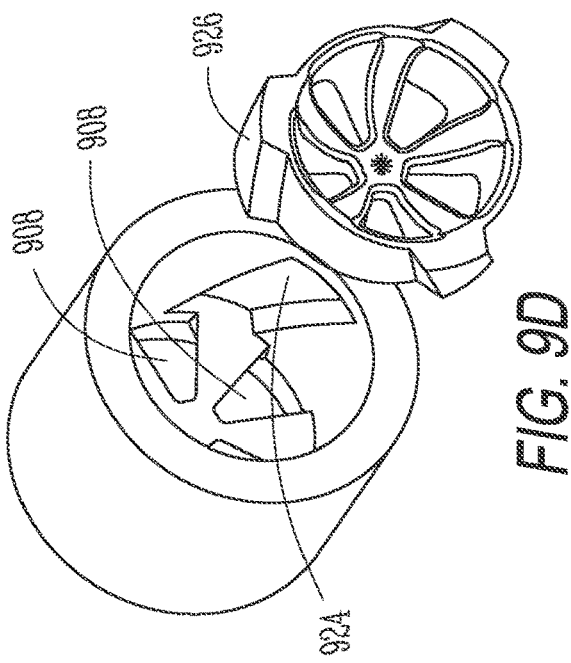
Figure 9A:
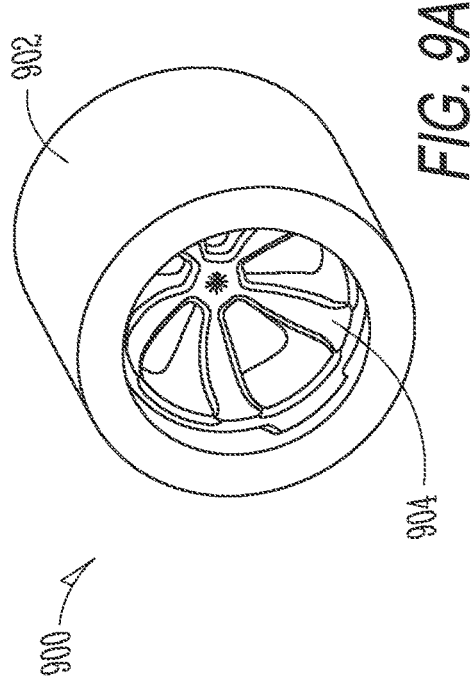
Figure 9C:
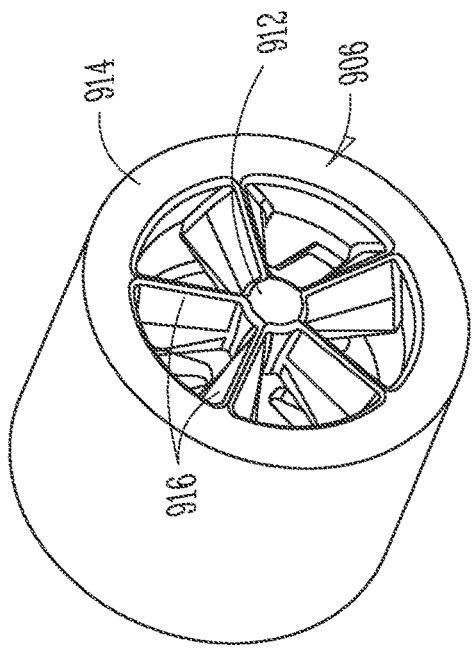
Figure 9F:
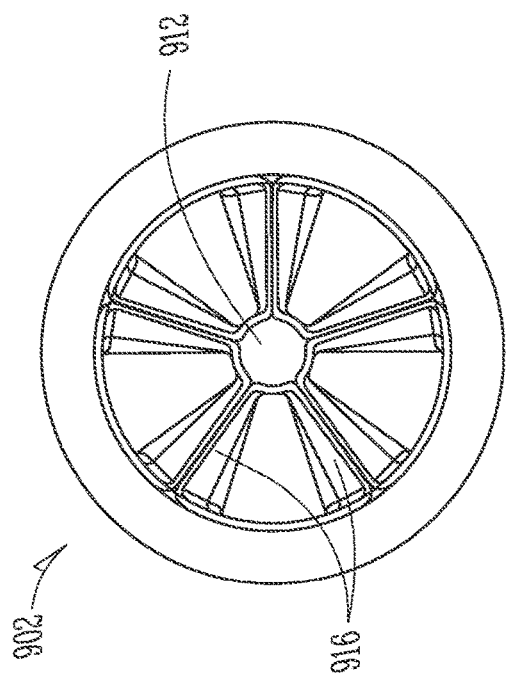
Figure 9H:
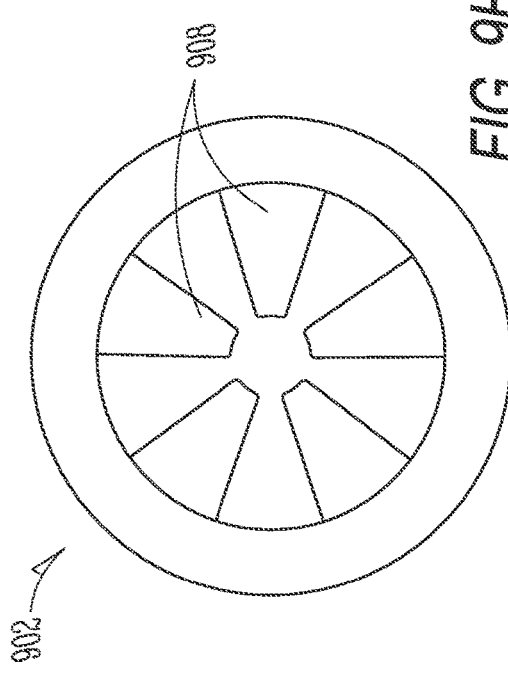
Figure 9E:
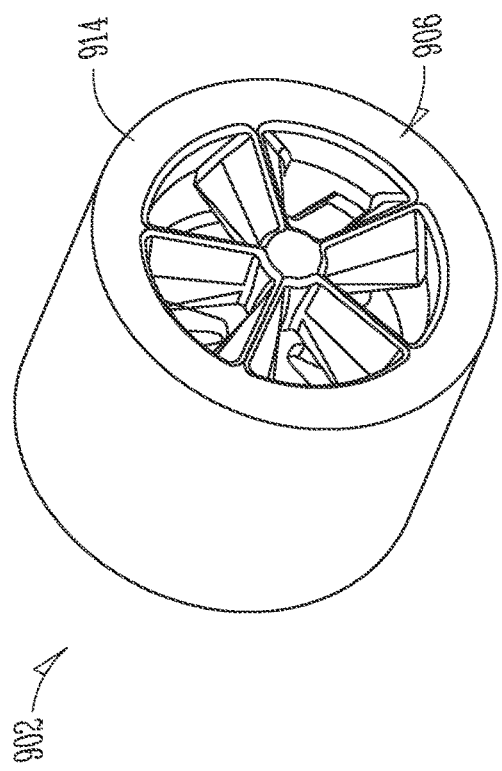
Figure 9G:
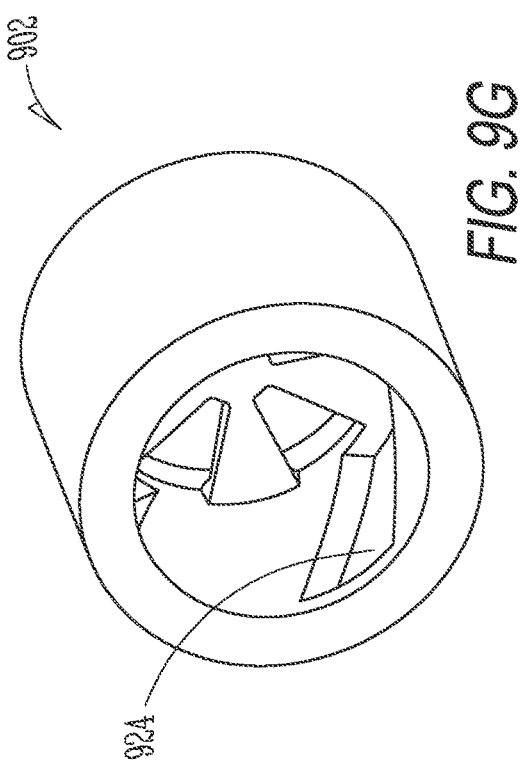

FIGS. 8A and 8B depict another example valve 800 in accordance with this disclosure. Rotary valve 800 is very similar in structure and function to rotary valve 700, except that instead of nested tubular outer and inner rotors 704 and 706 as with valve 700, valve 800 includes end-on tubular rotors 802 and 804 actuated by armatures 806 and 808 to rotate the rotors to control the flow of fluid through conduit 810. Rotor 802 includes aperture 812 and rotor 804 includes aperture 814. In other examples, rotors 802 and 804 could include more than one aperture each, including two, like in the example of valve 200, or four like the example of the valve 100.

FIGS. 9A-9L depict another example rotary valve 900 in accordance with this disclosure. FIGS. 9A-9D depict valve 900 assembled and exploded in a number of views. FIGS. 9E-9H depict stator 902 of valve 900 and FIGS. 9I-9L depict rotor 904 of valve 900.

As with other example rotary valves described herein, although not specifically depicted for described below, valve 900 can be disposed with respect to a conduit, actuated, and controlled in a manner consistent with that described above with reference to the example of valve 500 of FIG. 5, with the appropriate modifications for valve 900 and the intended application thereof. In the case of valve 900, for example, the valve can be arranged within or along a fluid conduit with a flow passage approximately sized to the diameter of valve 900 and can be actuated by one or more electrical armatures or other actuation mechanisms and controlled by a hardware, software, or hardware and software based electronic control device or system.

Rotary valve 900 includes stator 902 and rotor 904. Rotor 904 is disposed within and configured to rotate relative to stator 902. Rotor 904 is also configured to translate axially relative to stator 902, as described in more detail below.

Stator 902 is an annular, in this example cylindrical tubular member with an open end and partially closed end 906. Partially closed end 906 of stator 902 can be described as formed as a disc, as with other examples described above, including a number of apertures 908. Similarly, rotor 904 can be described as formed as a disc including a number of apertures 910. The overall structure and configuration of partially closed end 906 of stator 902 and stator 904 is, as evident from FIGS. 9A-9L, similar to an automobile wheel rim. For example, partially closed end 906 includes hub 912 aligned with a center of the end, rim 914 defining a circumference or outer periphery, and a number of spokes 916, each of which extend between the hub and the rim. Each of apertures 908 is defined by a space between adjacent spokes 916 and between hub 912 and rim 914 of partially closed end 906 of stator 902. Rotor 904 includes hub 918 aligned with the center of the rotor, rim 920 defining a circumference or outer periphery, and a number of spokes 922, each of which extend between the hub and the rim. Each of apertures 910 of rotor 904 is defined by a space between adjacent spokes 922 and between hub 918 and rim 920 of rotor 904. This hub, rim and spoke structure/nomenclature of valve 900 is also applicable to the rotors and stators of example valves 500, 600, 700 and 800.

Stator 902 also includes a number of grooves 924 in the inner surface thereof. In the example of FIGS. 9A-9L, stator 902 includes three grooves, but, in other examples, the stator could include more or fewer grooves. Grooves 924 extend axially along the inner surface of stator 902 along a curved path. In some cases, grooves 924 can extend axially along the inner surface of stator 902 along a helical path. Rotor 904 includes a number of flanges 926, which extend radially outward from the periphery (for example, outward from rim 920) of the rotor. Additionally, as best seen in FIGS. 9I-9L, flanges 926 have a curved, e.g., helical axial profile from one end of rotor 904 to the opposite end.

Rotary valve 900 can be actuated to rotate rotor 904 relative to stator 902 in a variety of ways. Regardless of the actuation mechanism, however, rotary valve 900 is configured to be actuated to cause rotor 904 to rotate and translate axially into multiple positions. For example, rotary valve 900 is configured to be actuated to cause rotor 904 to rotate and translate axially into a closed position in which rotor 904 is adjacent and abutting partially closed end 906 of stator 902 and spokes 916 of stator 902 align with apertures 910 of rotor 904 to substantially stop fluid flow through the rotary valve. Additionally, rotary valve 900 is configured to be actuated to cause rotor 904 to rotate and translate axially into an open position in which rotor 904 is axially offset from partially closed end 906 of stator 902 and apertures 908 of stator 902 are at least partially aligned with apertures 910 of rotor 904 to allow fluid flow through rotary valve 900.

In one example, rotary valve 900 is passively actuated. For example, rotary valve 900 can be arranged at least partially within and operatively connected to a fluid conduit. Rotary Rotor 904 can be actuated to rotate and translate axially relative to and within stator 902 by a pressure differential on either side of valve 900.

In another example, rotary valve 900 is actively actuated. For example, electrically conductive coils or an electrically conductive material can be embedded in, coupled to or formed integral with spokes 916 of stator 902 and a magnetic material can be embedded in, coupled to or formed integral with spokes 922 of rotor 904. The coils in spokes 916 of stator 902 can be coupled to a power source to selectively and controllably drive current through the coils (e.g., using a controller like controller 150 as described with reference to the example of FIG. 1) to actuate valve 900 to cause rotor 904 to rotate and translate axially relative to and within stator 902 to open and close the valve.

In an example, stator 902 could include two, opposite partially closed ends, each of which includes a hub, rim and spoke structure similar to that described above with reference to partially closed end of stator 902. As with other examples described above (and equally applicable as appropriate to examples described below), directionality (polarity) and the amount of current in the electric coils of spokes 916 of stator 902 will affect the force of attraction/repulsion between the electric coil and magnetic spokes 922 of rotor 904. The electric coils of stationary spokes 916 can thereby be used to actuate rotor 904, which allows for position and velocity control of rotor 904.

In order to improve and/or modulate fluid flow characteristics across rotary valve 900, spokes 916 of stator 902 and spokes 922 of rotor 904 are formed, at least in part, as airfoils. Forming spokes (or other solid structures in the path of fluid flow) as airfoils or other contoured shapes can improve pressure, velocity and other characteristics (e.g., boundary layer conditions) of fluid flow across rotary valves in accordance with this disclosure. Improving and/or modulating fluid flow characteristics using the structure of the valve may be advantageous in a number of different applications. For example, in medical applications the imposition of a valve including one or more solid structures in the flow path may cause blood flowing there through to be damaged (e.g., at a cellular level) or have some other untoward effect. Thus, forming spokes 916 of stator 902 and spokes 922 of rotor 904 are formed, at least in part, as airfoils may diminish such effects. Additionally, spokes 916 and/or spokes 922 of valve 900 may be designed/optimized to target some beneficial flow characteristic, including reducing pressure loss, boundary layer flow, or some other beneficial characteristic of the fluid flow as it passes through the valve.

Figure 10A:
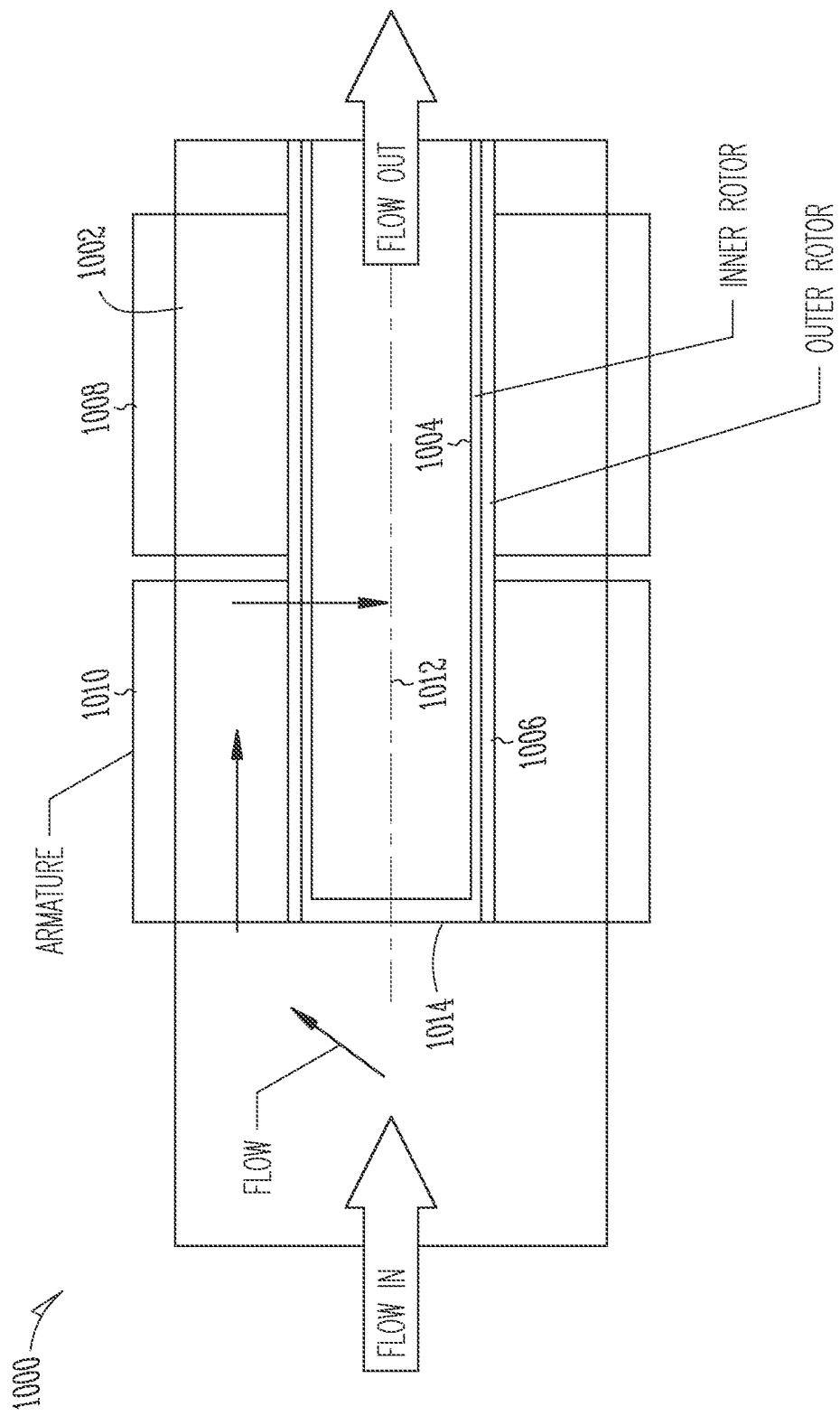
FIG. 10A depicts another example rotary valve in accordance with this disclosure.
Figure 10B:
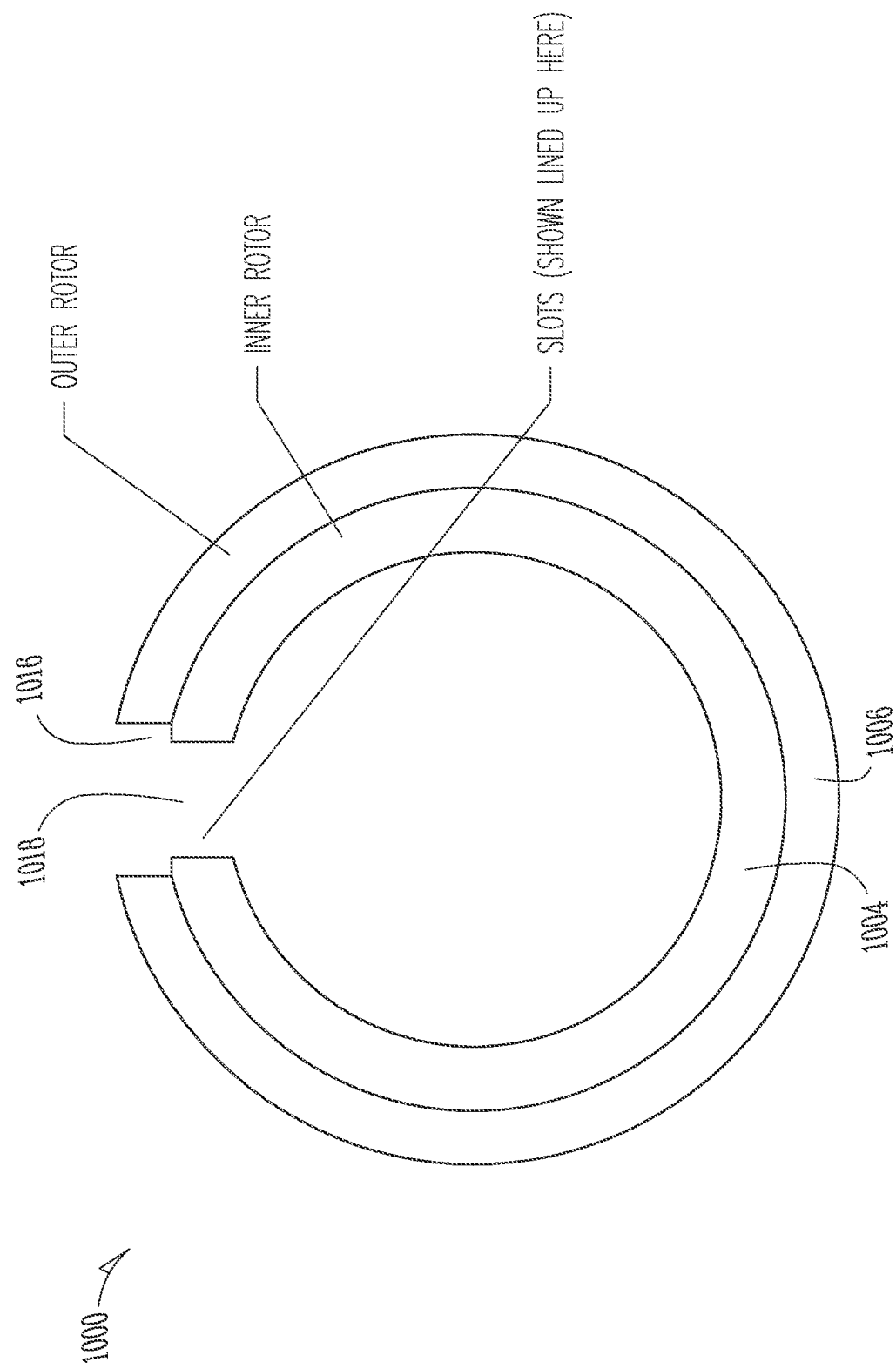
FIG. 10B depicts the inner and outer rotor of the rotary valve of FIG. 10A.

FIG. 10A depicts another example rotary valve 1000 operatively coupled and configured to control fluid flow through conduit 1002. FIG. 10B depicts inner rotor 1004 and outer rotor 1006 of rotary valve 1000. In the example of FIGS. 10A and 10B, rotary valve 1000 includes inner rotor 1004, outer rotor 1006, inner rotor armature 1008, and outer rotor armature 1010. Valve 1000 is configured to be actuated by one or both of armatures 1008 and 1010 to rotate one or both of rotors 1004 and 1006 about axis 1012 (axis of rotation of rotors/valve and longitudinal axis of conduit) to control flow of a fluid through conduit 1002.

Outer rotor 1004 and inner rotor 1006 are what may be referred to as nested tubular rotors. Outer rotor 1006 is an annular, in this example cylindrical tubular member with an open end and completely closed end 1014. Outer rotor 1004 also includes aperture, in this example a longitudinal slot 1016 in the outer circumference of the rotor. Inner rotor 1004 is also an annular, in this example cylindrical tubular member with two open ends. Inner rotor 1004 includes an aperture, in this example a longitudinal slot 1018 in the outer circumference of the rotor. In other examples, inner rotor 1004 and outer rotor 1006 could include multiple apertures, for example, multiple slots. Slots 1016 and 1018 in outer rotor 1004 and inner rotor 1006 can be straight or linear, or, in other examples, the longitudinal slots can have a curved profile, including, e.g., a hyperbolic, parabolic and elliptic.

Inner rotor 1004 is nested or received in outer rotor 1006. Inner rotor 1004 extends beyond and is longer than outer rotor 1006 and the nested outer and inner rotors of example rotary valve 1000 are disposed in and along the flow path of fluid conduit 1002.

Each of rotors 1004 and 1006 include a magnetic core or are formed at least in part from a magnetic material. Magnetic cores of rotors 1004 and 1006 can be a separate component coupled to each rotor or can be formed integral therewith.

Rotary valve 1000 is configured to be actively actuated by one or both of armatures 1008 and 1010 being energized to rotate one or both of inner rotor 1004 and outer rotor 1006. As with other example valves in accordance with this disclosure, each of rotors 1004 and 1006 can be controllably actuated to rotate in one or two directions and at a constant or variable angular velocity. Additionally, each of rotors 1004 and 1006 can rotate at the same speed in the same directions or at different speeds in different directions, or at the same speeds in different directions or at different speeds in the same direction.

The angular velocity of rotors 1004 and 1006 can be selected to produce a target frequency pulsatile flow through conduit 1002, given the number and size of apertures 1016 and 1018. As aperture 1016 in rotor 1006 rotates into alignment with aperture 1018 in rotor 1004, fluid can flow through valve 1000 and conduit 1002. As aperture 1016 in rotor 1006 rotates out of alignment with aperture 1018 in rotor 1004, fluid flow through valve 1000 and conduit 1002 is stopped.

NOTES & EXAMPLES

The present application provides for the following exemplary embodiments or examples, the numbering of which is not to be construed as designating levels of importance:

Example 1 provides a medical device comprising: a constant-flow fluid pump configured to pump a fluid through a fluid conduit; and a rotary valve fluidically connected to the pump, the rotary valve comprising: a first valve member configured to be disposed at least partially within the fluid conduit and comprising at least one first aperture; a second valve member configured to be disposed at least partially within the fluid conduit and comprising at least one second aperture, and at least one of the first and second valve members being rotatable, the first and second valve members being configured to be positioned in a plurality of positions relative to one another, and a position of the at least one first aperture relative to the at least one second aperture controlling fluid flow through the rotary valve.

Example 2 provides the medical device of Example 1 and optionally further comprising an artificial lung device fluidically coupled to the pump and the rotary valve.

Example 3 provides the medical device of Example 1 and optionally further comprising a dialyser device fluidically coupled to the pump and the rotary valve.

Example 4 provides the medical device of Example 1 and optionally further comprising: a second constant-flow fluid pump; and a second rotary valve fluidically connected to the pump via a fluid conduit and configured to control fluid flow through the fluid conduit.

Example 5 provides the medical device of Examples 1-4 and optionally wherein the at least one of the first and second valve members being rotatable is configured to rotate periodically.

Example 6 provides the medical device of Examples 1-4 and optionally wherein the at least one of the first and second valve members being rotatable is configured to rotate continuously.

Example 7 provides the medical device of Examples 1-4 and optionally wherein the at least one of the first and second valve members being rotatable is configured to rotate in one or more directions.

Example 8 provides the medical device of Examples 1-7 and optionally wherein the at least one of the first and second valve members being rotatable is configured to be rotated to be positioned in one or more first positions in which the at least one first aperture and the at least one second aperture are at least partially aligned to allow fluid to flow through the rotary valve and a second position in which the at least one first aperture and the at least one second apertures are unaligned to substantially stop fluid flow through the rotary valve.

Example 9 provides the medical device of Examples 1-8 and optionally wherein the at least one of the first and second valve members being rotatable is configured to be rotated to be positioned in a first position in which the at least one first aperture and the at least one second aperture are at least partially aligned at a first time and a second position in which the at least one first aperture and the at least one second aperture are at least partially aligned at a first time to vary the volumetric or mass flow rate through the rotary valve.

Example 10 provides the medical device of Examples 1-9 and optionally wherein: the first valve member comprises a stator; and the second valve member comprises a rotor; and the second valve member is rotatable relative to the first valve member.

Example 11 provides the medical device of Example 10 and optionally wherein the stator comprises an annulus comprising an open end and a second end comprising a first disc and the rotor comprises a second disc disposed and configured to rotate within the annulus adjacent the first disc, the first disc comprising the at least one first aperture and the second disc comprising the at least one second aperture.

Example 12 provides the medical device of Example 10 and optionally wherein the rotor comprises an annulus comprising an open end and a second end comprising a first disc and the stator comprises a second disc disposed adjacent the first disc, the first disc comprising the at least one first aperture and the second disc comprising the at least one second aperture.

Example 13 provides the medical device of Examples 11-12 and optionally wherein each of the first and second discs comprise: a hub aligned with a center of the disc; a rim defining a circumference of the disc; and a plurality of spokes, each of which extend between the hub and the rim, wherein the at least one first aperture comprises a plurality of first apertures, each of which is defined by a space between adjacent spokes and between the hub and the rim of the first disc, and wherein the at least one second aperture comprises a plurality of second apertures, and wherein a space between adjacent spokes and between the hub and the rim of the second disc defines one of the plurality of first apertures.

Example 14 provides the medical device of Example 13 and optionally wherein the annulus comprises at least one groove on an inner surface thereof, and wherein the second disc comprises at least one flange extending radially outward from a periphery of the second disc, the at least one flange received within the at least one groove.

Example 15 provides the medical device of Example 14 and optionally wherein the at least one groove extends axially from adjacent the first disc along a curved path.

Example 16 provides the medical device of Example 14 and optionally wherein the second disc is configured to rotate and translate axially relative to the first disc.

Example 17 provides the medical device of Example 14 and optionally wherein the second disc is configured to rotate and translate axially relative to the first disc into a closed position in which the second disc is adjacent the first disc and the plurality of spokes of the second disc align with the plurality of first apertures of the first disc to substantially stop fluid flow through the rotary valve and cause the second disc to rotate and translate axially into an open position in which the second disc is axially offset from the first disc and the plurality of second apertures of the second disc are at least partially aligned with the plurality of first apertures of the first disc to allow fluid flow through the rotary valve.

Example 18 provides the medical device of Examples 1-9 and optionally wherein: the first valve member comprises a first rotor; and the second valve member comprises a second rotor; and the first and second valve members are rotatable relative to one another.

Example 19 provides the medical device of Example 18 and optionally wherein: the first rotor comprises an annulus comprising an open end and a second end comprising a first disc, the first disc comprising the at least one first aperture; and the second rotor comprises an annulus comprising an open end and a second end comprising a second disc, the second disc comprising the at least one second aperture.

Example 20 provides the medical device of Example 19 and optionally wherein the second rotor is arranged within the annulus of the first rotor, the second disc being arranged adjacent the first disc.

Example 21 provides the medical device of Example 19 and optionally wherein the first and second rotors are disposed in an end-on arrangement with the first and second discs facing and adjacent one another and the first and second rotors axially aligned.

Example 22 provides the medical device of Examples 19-21 and optionally wherein the first rotor is identical to the second rotor.

Example 23 provides the medical device of Example 18 and optionally wherein: the first rotor comprises an annulus comprising two open ends; the at least one first aperture comprises a longitudinal slot in a circumference of the first rotor; the second rotor comprises an annulus comprising an open end and a closed end; and the at least one second aperture comprises a longitudinal slot in a circumference of the second rotor.

Example 24 provides the medical device of Examples 1-23 and optionally wherein the structure of the first valve member is identical to the structure of the second valve member.

Example 25 provides the medical device of Examples 1-24 and optionally further comprising an actuator, the actuator configured to rotate at least one of the first and second valve members to cause the valve members to be positioned in the plurality of positions relative to one another to control flow of the fluid through the conduit.

Example 26 provides the medical device of Example 25 and optionally wherein the actuator comprises a mechanical, electrical, electro-mechanical, or electromagnetic actuator.

Example 27 provides the medical device of Examples 1-24 and optionally wherein the valve is a passive valve, wherein a pressure differential between first and second sides of the rotary valve cause at least one of the first and second valve members to rotate to be positioned in a plurality of positions relative to one another.

Example 28 provides a method of replacing at least one function of a human organ, the method comprising: coupling an inlet side of a constant-flow pump to a body of a human patient via a fluid conduit; coupling an outlet side of the pump to a rotary valve via the conduit, the rotary valve comprising at least one rotatable valve member configured to rotate relative to the conduit, the at least one rotatable valve member comprising at least one aperture; and coupling the rotary valve to the body of the patient via the conduit; pumping, by the pump, fluid from the body of the patient through the conduit and the rotary valve and back into the body.

Various examples according to this disclosure have been described. These and other examples are within the scope of the following claims.

What is claimed is:

1. A medical device comprising:
   a constant-flow fluid pump configured to pump a fluid through a fluid conduit;
   a rotary valve fluidically connected to the pump, the rotary valve comprising:
   a stator disposed at least partially within the fluid conduit and comprising at least one first aperture;
   a rotor disposed at least partially within the fluid conduit and comprising at least one second aperture, the rotor being rotatable relative to the stator, the rotor being configured to be positioned in a plurality of positions relative to the stator, and a position of the at least one first aperture relative to the at least one second aperture controlling fluid flow through the rotary valve;
   an actuator configured to rotate the rotor to cause the rotor to be positioned in the plurality of positions relative to the stator; and
   a controller operatively connected to and controlling the actuator to cause the rotor to rotate continuously to produce a pulsatile flow of the fluid through the conduit by varying the angular velocity of the rotor over time.

2. The medical device of claim 1, further comprising an artificial lung device fluidically coupled to the pump and the rotary valve.

3. The medical device of claim 1, further comprising a dialyser device fluidically coupled to the pump and the rotary valve.

4. The medical device of claim 1 further comprising:
   a second constant-flow fluid pump; and
   a second rotary valve fluidically connected to the second constant-flow pump via a fluid conduit and configured to control fluid flow through the fluid conduit.

5. The medical device of claim 1, wherein the rotor is configured to be rotated to be positioned in one or more first positions in which the at least one first aperture and the at least one second aperture are at least partially aligned to allow fluid to flow through the rotary valve and a second position in which the at least one first aperture and the at least one second apertures are unaligned to substantially stop fluid flow through the rotary valve.

6. The medical device of claim 1, wherein the rotor is configured to be rotated to be positioned in a first position in which the at least one first aperture and the at least one second aperture are at least partially aligned at a first time and a second position in which the at least one first aperture and the at least one second aperture are at least partially aligned at a first time to vary the volumetric or mass flow rate through the rotary valve.

7. The medical device of claim 1, wherein the stator comprises an annulus comprising an open end and a second end comprising a first disc and the rotor comprises a second disc disposed and configured to rotate within the annulus adjacent the first disc, the first disc comprising the at least one first aperture and the second disc comprising the at least one second aperture.

8. The medical device of claim 7, wherein each of the first and second discs comprise:
   a hub aligned with a center of the disc;
   a rim defining a circumference of the disc; and
   a plurality of spokes, each of which extend between the hub and the rim,
   wherein the at least one first aperture comprises a plurality of first apertures, each of which is defined by a space between adjacent spokes and between the hub and the rim of the first disc, and
   wherein the at least one second aperture comprises a plurality of second apertures, and wherein a space between adjacent spokes and between the hub and the rim of the second disc defines one of the plurality of first apertures.

9. The medical device of claim 8, wherein the annulus comprises at least one groove on an inner surface thereof, and wherein the second disc comprises at least one flange extending radially outward from a periphery of the second disc, the at least one flange received within the at least one groove.

10. The medical device of claim 9, wherein the at least one groove extends axially from adjacent the first disc along a curved path.

11. The medical device of claim 9, wherein the second disc is configured to rotate and translate axially relative to the first disc.

12. The medical device of claim 9, wherein the second disc is configured to rotate and translate axially relative to the first disc into a closed position in which the second disc is adjacent the first disc and the plurality of spokes of the second disc align with the plurality of first apertures of the first disc to substantially stop fluid flow through the rotary valve and cause the second disc to rotate and translate axially into an open position in which the second disc is axially offset from the first disc and the plurality of second apertures of the second disc are at least partially aligned with the plurality of first apertures of the first disc to allow fluid flow through the rotary valve.

13. The medical device of claim 1, wherein the rotor comprises an annulus comprising an open end and a second end comprising a first disc and the stator comprises a second disc disposed adjacent the first disc, the first disc comprising the at least one first aperture and the second disc comprising the at least one second aperture.

14. The medical device of claim 1, wherein the pulsatile flow of the fluid through the conduit mimics a pulsatile blood flow produced naturally by a human heart.

15. The medical device of claim 1, wherein the actuator comprises:
 at least one electrical armature connected to a power source and configured to receive a constant or variable electrical current therefrom; and
 at least one magnetic member coupled to or integral with the rotor, the at least one electrical armature surrounding the at least one magnetic member.

16. The medical device of claim 1, wherein the actuator is configured to cause the rotor to rotate at a constant angular velocity.

17. The medical device of claim 1, wherein the actuator is configured to cause the rotor to rotate at a variable angular velocity.

18. A method of replacing at least one function of a human organ, the method comprising:
 coupling an inlet side of a constant-flow pump to a body of a human patient via a fluid conduit;
 coupling an outlet side of the pump to a rotary valve via the conduit, the rotary valve comprising at least one rotatable valve member configured to rotate relative to the conduit, the at least one rotatable valve member comprising at least one aperture;
 coupling the rotary valve to the body of the patient via the conduit;
 pumping, by the pump, fluid from the body of the patient through the conduit and the rotary valve; and
 varying an angular velocity of the at least one rotatable valve member over time to produce a pulsatile flow of the fluid out of the rotary valve and back into the body.

19. An apparatus for creating pulsatile flow, the apparatus comprising:
 a constant-flow fluid pump configured to pump a fluid through a fluid conduit;
 a rotary valve fluidically connected to the pump, the rotary valve comprising:
 a first valve member configured to be disposed within the fluid conduit and comprising at least one first aperture;
 a second valve member configured to be disposed within the fluid conduit and comprising at least one second aperture, and
 at least one of the first and second valve members being rotatable, the first and second valve members being configured to be positioned in a plurality of positions relative to one another, and a position of the at least one first aperture relative to the at least one second aperture controlling fluid flow through the rotary valve;
 an actuator configured to rotate at least one of the first and second valve members to cause the valve members to be positioned in the plurality of positions relative to one another; and
 a controller operatively connected to and controlling the actuator to cause the at least one of the first and second valve members to rotate continuously to produce a pulsatile flow of the fluid through the conduit by varying the angular velocity of the at least one of the first and second valve members over time.

20. The apparatus of claim 19, wherein:
the first valve member comprises a stator;
the second valve member comprises a rotor; and
the second valve member is rotatable relative to the first valve member.

21. The apparatus of claim 19, wherein:
the first valve member comprises a first rotor;
the second valve member comprises a second rotor; and
the first and second valve members are rotatable in the same direction and independent of one another.

22. The apparatus of claim 21, wherein:
the first rotor comprises an annulus comprising an open end and a second end comprising a first disc, the first disc comprising the at least one first aperture; and
the second rotor comprises an annulus comprising an open end and a second end comprising a second disc, the second disc comprising the at least one second aperture.

23. The apparatus of claim 22, wherein the second rotor is arranged within the annulus of the first rotor, the second disc being arranged adjacent the first disc.

24. The apparatus of claim 22, wherein the first and second rotors are disposed in an end-on arrangement with the first and second discs facing and adjacent one another and the first and second rotors axially aligned.

25. The apparatus of claim 21, wherein:
the first rotor comprises an annulus comprising two open ends;
the at least one first aperture comprises a longitudinal slot in a circumference of the first rotor;
the second rotor comprises an annulus comprising an open end and a closed end; and
the at least one second aperture comprises a longitudinal slot in a circumference of the second rotor.

26. The apparatus of claim 21, wherein:
the first rotor comprises a first disc comprising the at least one first aperture; and
the second rotor comprises a second disc comprising the at least one second aperture.

27. The apparatus of claim 26, wherein:
the first disc comprises two apertures arranged approximately opposite one another about a center of the first disc; and
the second disc comprises two apertures arranged approximately opposite one another about a center of the second disc.

* * * * *

UNITED STATES PATENT AND TRADEMARK OFFICE
CERTIFICATE OF CORRECTION

PATENT NO. : 11,324,942 B2
APPLICATION NO. : 16/312705
DATED : May 10, 2022
INVENTOR(S) : Ratner et al.

It is certified that error appears in the above-identified patent and that said Letters Patent is hereby corrected as shown below:

On the Title Page

Item (73), in "Assignee", in Column 1, Line 1, delete "RATHER," and insert --RATNER,-- therefor Item (73), in "Assignee", in Column 1, Line 2, delete "BRAMA," and insert --BHAMA,-- therefor On page 2, in Column 2, under "Other Publications", Line 2, delete "Oct. 31," and insert --Jan. 10,-- therefor On page 2, in Column 2, under "Other Publications", Line 5, delete "Oct. 31," and insert --Jan. 10,-- therefor In the Specification In Column 7, Line 44, delete "150." and insert --510.-- therefor In Column 8, Line 32, delete "506" and insert --508-- therefor In Column 8, Line 48, delete "506" and insert --508-- therefor In Column 12, Line 33, delete "stator" and insert --rotor-- therefor In Column 12, Line 41, after "902.", insert a linebreak In Column 14, Line 7, delete "1004" and insert --1006-- therefor In Column 14, Line 7, delete "1006" and insert --1004-- therefor In Column 14, Line 10, delete "1004" and insert --1006-- therefor Signed and Sealed this
Eighteenth Day of October, 2022

Katherine Kelly Vidal
*Director of the United States Patent and Trademark Office*

In Column 14, Line 19, delete "1004" and insert --1006-- therefor

In Column 14, Line 19, delete "1006" and insert --1004-- therefor